(12) United States Patent
Mori

(10) Patent No.: US 7,583,778 B2
(45) Date of Patent: Sep. 1, 2009

(54) X-RAY CT APPARATUS AND X-RAY CT BACKPROJECTION OPERATING METHOD

(75) Inventor: Issei Mori, Sendai (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 228 days.

(21) Appl. No.: 10/895,858

(22) Filed: Jul. 22, 2004

(65) Prior Publication Data

US 2005/0058239 A1 Mar. 17, 2005

(30) Foreign Application Priority Data

Jul. 24, 2003 (JP) ............... P2003-201332

(51) Int. Cl.
*A61B 6/03* (2006.01)

(52) U.S. Cl. .......................................... 378/4
(58) Field of Classification Search ............ 378/4, 378/19, 205, 901
See application file for complete search history.

(56) References Cited

U.S. PATENT DOCUMENTS 4,176,279 A * 11/1979 Schwierz et al. ............... 378/4

(Continued)

FOREIGN PATENT DOCUMENTS

EP 0 239 647 A1 10/1987

(Continued)

OTHER PUBLICATIONS

Hsieh, Investigation of 3D Image Artifact Caused by Projection Weighting and Misalignment, Proceedings of the 6th International Conference on Image Processing (ICIP'99), Oct. 1999, vol. 2, pp. 681-685.*

(Continued)

*Primary Examiner*—Edward J Glick
*Assistant Examiner*—John M Corbett
(74) *Attorney, Agent, or Firm*—Oblon, Spivak, McClelland, Maier & Neustadt, P.C.

(57) ABSTRACT

An X-ray CT apparatus is provided which can be suppressed or eliminated of aliasing occurrence in the R-R scheme. The X-ray CT apparatus has a reconstructing device for processing the collected data on each view to thereby obtain projection data and making a backprojection operation on the projection data to thereby reconstruct an image. In the reconstructing device, when the X-ray detector element closest to a rotation center of the detector system determines that an X-ray path for detecting the X-ray irradiated is in a position deviated by a sampling offset (first value) from the rotation center, projection data of the X-ray detector element at least in a vicinity of the rotation center upon the backprojection operation is backprojected to a position deviated by a backprojection offset (second value: different from the first value) from the rotation center. Namely, in the case projection data has a deviation from a desired alignment state, backprojection is made to a suitably offset position correspondingly to the misalignment state without backprojection as per the projection path, thus achieving aliasing suppression and resolving power maintenance.

12 Claims, 12 Drawing Sheets

U.S. PATENT DOCUMENTS

| | | | |
|---|---|---|---|
| 4,637,040 A | | 1/1987 | Sohval et al. |
| 4,991,190 A | * | 2/1991 | Mori .......................... 378/9 |
| 5,307,264 A | * | 4/1994 | Waggener et al. ............. 378/14 |
| 5,432,339 A | * | 7/1995 | Gordon et al. ......... 250/231.13 |
| 5,768,331 A | | 6/1998 | Gordon et al. |
| 5,848,117 A | * | 12/1998 | Urchuk et al. ................ 378/19 |
| 6,332,013 B1 | * | 12/2001 | Hsieh .......................... 378/15 |
| 2003/0002617 A1 | * | 1/2003 | Hsieh et al. ................... 378/19 |

FOREIGN PATENT DOCUMENTS

| | | |
|---|---|---|
| EP | 0 543 626 A1 | 5/1993 |
| EP | 1 266 620 A2 | 12/2002 |
| JP | 53-126892 | 11/1978 |
| JP | 2003-24322 | 1/2003 |

OTHER PUBLICATIONS

Azevedo et al., Calculation of the Rotational Centers in Computed Tomography Sinograms, Aug. 1990, IEEE Transactions on Nuclear Science, vol. 37, No. 4, pp. 1525-1540.*

Concepcion et al., CT Fan Beam Reconstruction with a Nonstationary Axis of Rotation, Mar. 1992, IEEE Transactions on Medical Imaging, vol. 11, No. 1, pp. 111-116.*

Mori et al., Method for Suppressing Aliasing in CT, Sep. 2003, Medical Imaging Technology, vol. 21, No. 4, pp. 254-264.*

PTO 08-7343, English translation of Mori et al., Method for Suppressing Aliasing in CT, Sep. 2003, Medical Imaging Technology, vol. 21, No. 4, pp. 254-264.*

Lewitt, Reconstruction Algorithms: Transformation Methods, 1983, IEEE, vol. 71, No. 3, pp. 390-408.*

La Riviere et al.,Fourier-based approach to interpolation in single-slice helical computed tomography, Mar. 2001, Medical Physics, vol. 28, No. 3, pp. 381-392.*

La Riviere et al., Longitudinal Aliasing in Multislice Helical Computed Tomography: Sampling and Cone-Beam Effects, Nov. 2002, IEEE, vol. 21, No. 11, pp. 1366-1373.*

Carl R. Crawford, et al., "Reconstruction for fan beam with an angular-dependent displaced center-of-rotation", Medical Physics, XP-002303295, vol. 15, No. 1, Jan./Feb. 1998, pp. 67-71.

Huili Wang, et al., "Astigmatic single photon emission computed tomography imaging with a displaced center of rotation", Medical Physics, vol. 25, No. 8, XP-012010550, Aug. 1998, pp. 1493-1501.

Y. Iwai, et al., "Medical Imaging Equipment", Corona Publishing Co., LTD Dec. 20, 1998, pp. 10-13.

T. M. Peters, et al., "Computed Tomography with Fan Beam Geometry", Journal of Computer Assisted Tomography, vol. 1, No. 4, 1997, pp. 429-436.

Jiang Hsieh, "Investigation of 3D Image Artifact Caused by Projection Weighting and Misalignment", ICIP 99 IEEE (1999), vol. 2, pp. 681-685.

* cited by examiner

FIG. 1

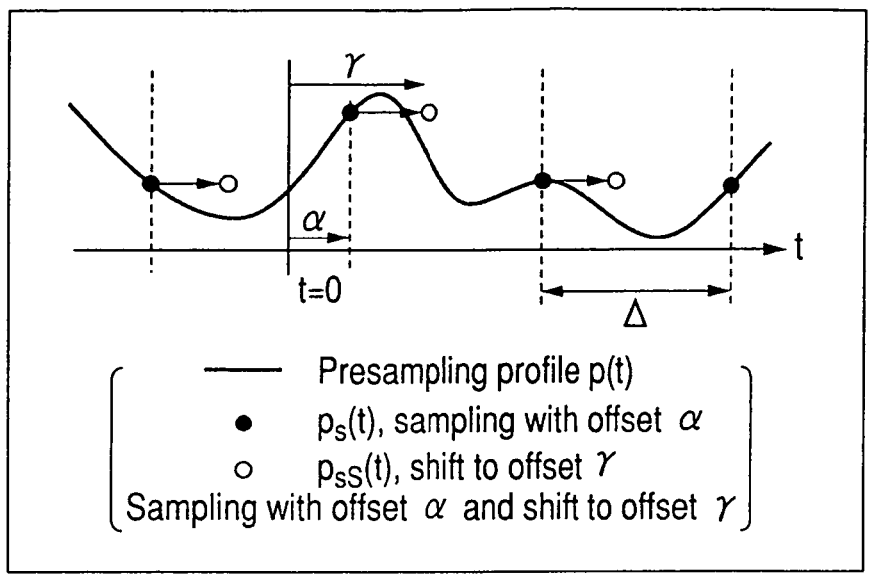

— Presampling profile p(t)
● $p_s(t)$, sampling with offset $\alpha$
○ $p_{sS}(t)$, shift to offset $\gamma$
Sampling with offset $\alpha$ and shift to offset $\gamma$

FIG. 2

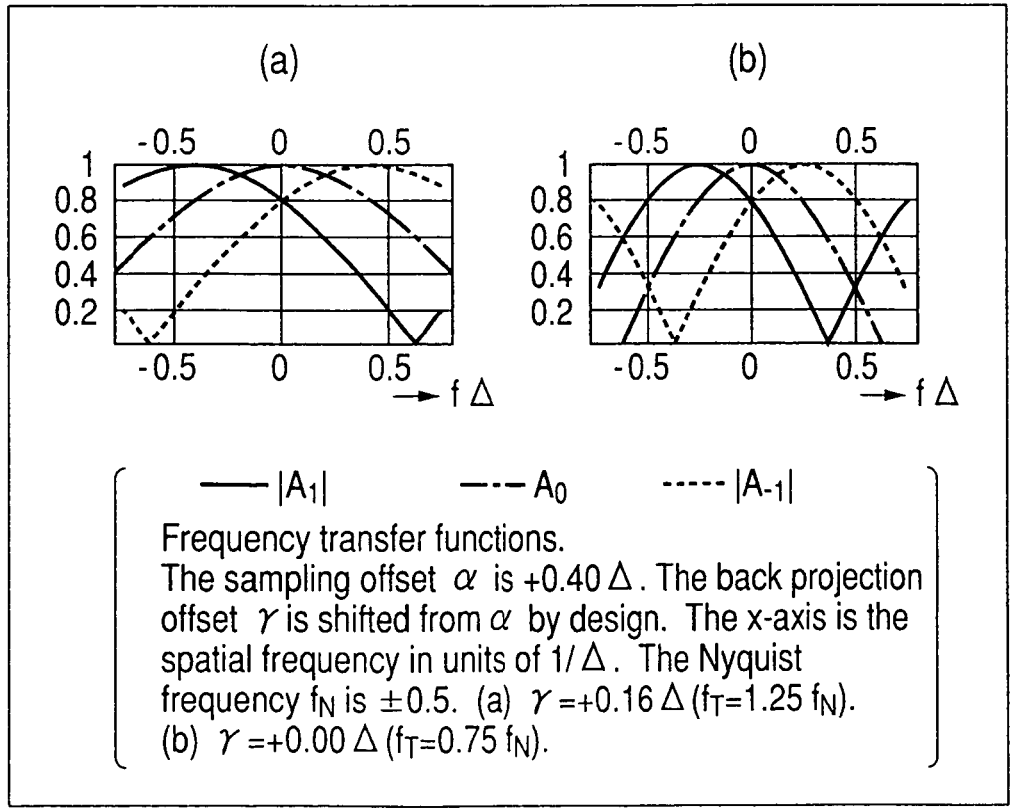

—— $|A_1|$   — — $A_0$   ····· $|A_{-1}|$

Frequency transfer functions.
The sampling offset $\alpha$ is +0.40 $\Delta$. The back projection offset $\gamma$ is shifted from $\alpha$ by design. The x-axis is the spatial frequency in units of 1/$\Delta$. The Nyquist frequency $f_N$ is ±0.5. (a) $\gamma$ =+0.16 $\Delta$ ($f_T$=1.25 $f_N$). (b) $\gamma$ =+0.00 $\Delta$ ($f_T$=0.75 $f_N$).

FIG. 3

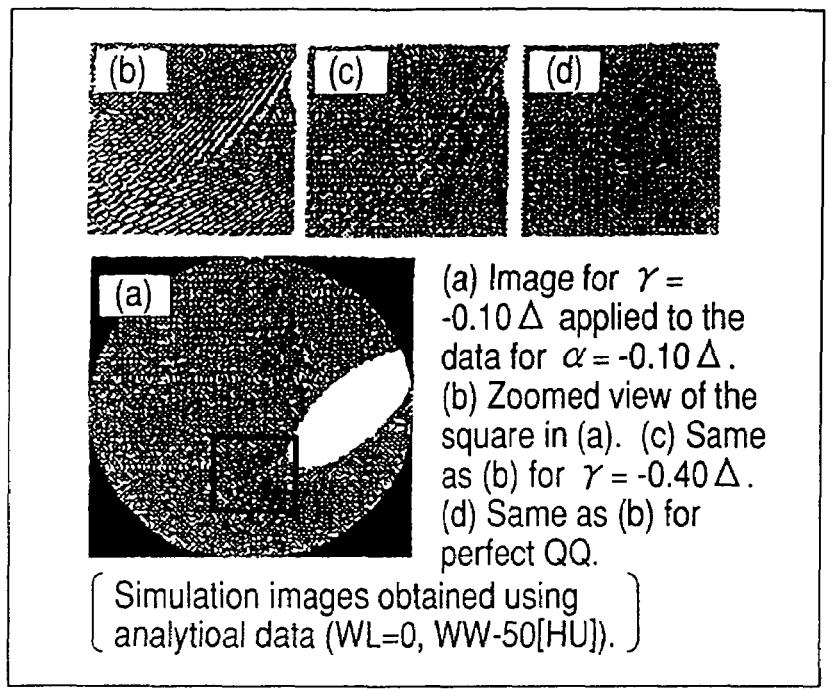

(a) Image for $\gamma = -0.10\,\Delta$ applied to the data for $\alpha = -0.10\,\Delta$.
(b) Zoomed view of the square in (a). (c) Same as (b) for $\gamma = -0.40\,\Delta$.
(d) Same as (b) for perfect QQ.

Simulation images obtained using analytioal data (WL=0, WW-50[HU]).

FIG. 4

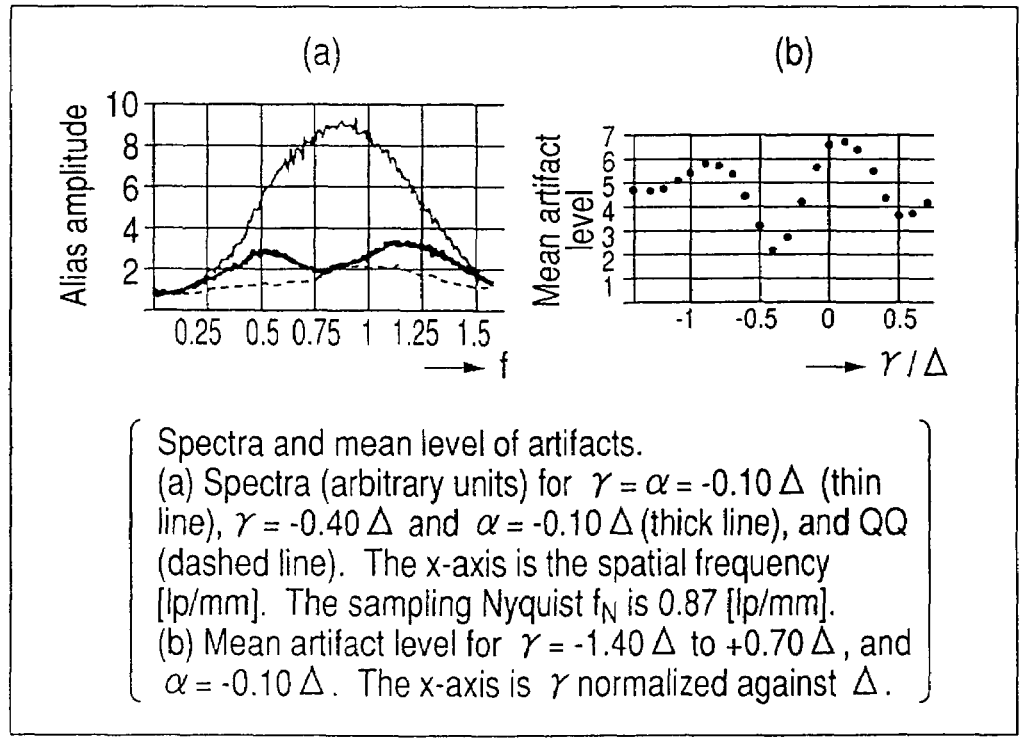

Spectra and mean level of artifacts.
(a) Spectra (arbitrary units) for $\gamma = \alpha = -0.10\,\Delta$ (thin line), $\gamma = -0.40\,\Delta$ and $\alpha = -0.10\,\Delta$ (thick line), and QQ (dashed line). The x-axis is the spatial frequency [lp/mm]. The sampling Nyquist $f_N$ is 0.87 [lp/mm].
(b) Mean artifact level for $\gamma = -1.40\,\Delta$ to $+0.70\,\Delta$, and $\alpha = -0.10\,\Delta$. The x-axis is $\gamma$ normalized against $\Delta$.

Alias artifact in conventional (non helical) scan (WL=so, WW=100[HU]).
(a) Entire image, $\gamma = \alpha = -0.414\Delta$. (b) Zoomed view of square in (a). (c) Nearly ideal QQ $\gamma = \alpha = -0.24\Delta$.
(d) $\gamma = -0.196\Delta$ ($f_T=1.5f_N$). (e) $\gamma = -0.152\Delta$ ($f_T=1.25f_N$).
(f) $\gamma = -0.086\Delta$ ($f_T=1.0f_N$). In (d), (e), and (f), the same projection data as in (a) are used.

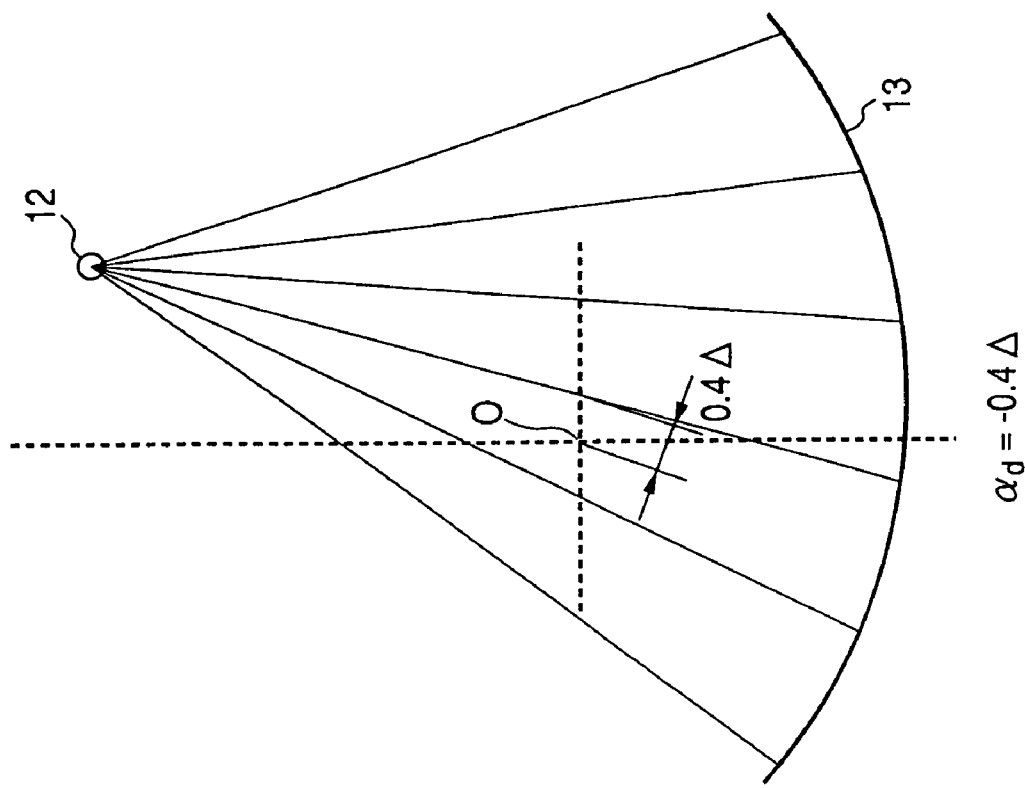
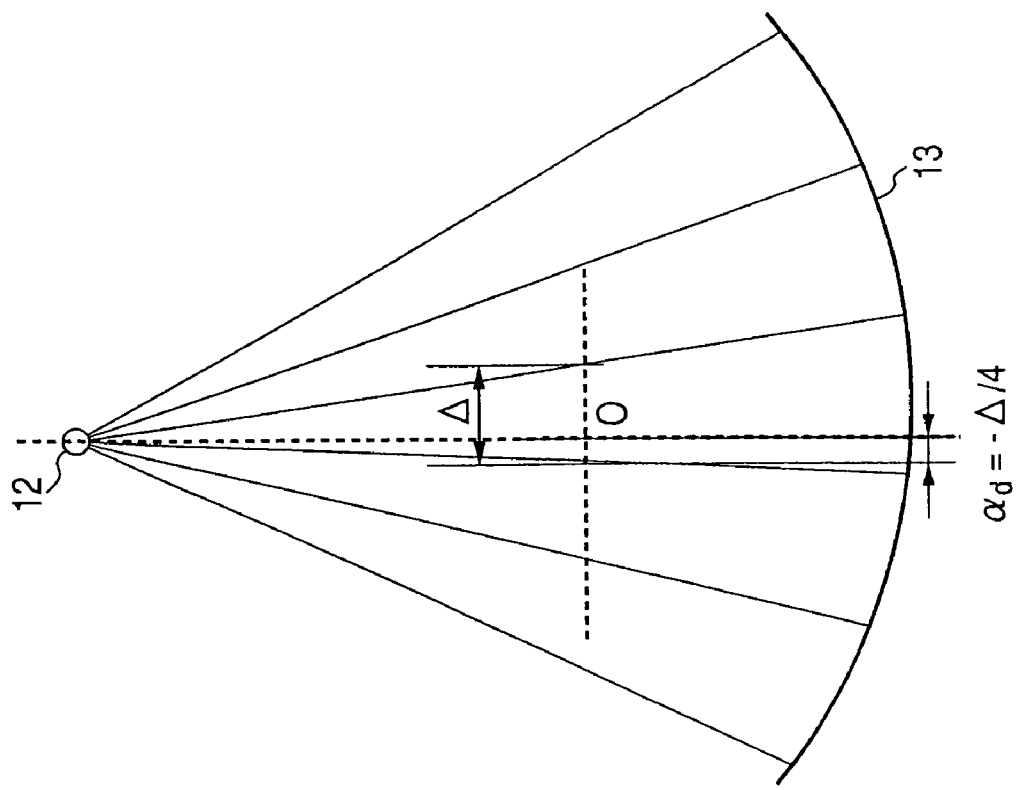
FIG. 9A
FIG. 9B $\gamma = +0.1 \Delta$ $\gamma_d = +0.1 \Delta$ $\gamma_d = +0.1 \Delta$

X-RAY CT APPARATUS AND X-RAY CT BACKPROJECTION OPERATING METHOD

BACKGROUND OF THE INVENTION

1. Field of the Invention

The present invention relates to an X-ray CT apparatus for irradiating an X-ray to a subject and collecting transmission data of the X-ray, to obtain an image about an internal structure of the subject from the collected data.

2. Description of the Related Art

Today, the most representative radiodiagnostic apparatuses include X-ray CT (Computed Tomography) apparatuses. The X-ray CT apparatuses are classified into various forms according to the collection scheme of projection data.

There is an R-R scheme (rotate-rotate or third generation scheme) as one of the data collection forms. The R-R scheme is a scheme oppositely arranged with an X-ray tube and an X-ray detector in a state spatially sandwiching a subject, to perform data collection while rotating the X-ray tube and the X-ray detector in unison round the subject. Namely, when the X-ray tube and the X-ray detector are rotated in unison round the subject, projection data is gathered in views at a constant angular interval (at an interval of sampling points).

The R-R-schemed X-ray CT apparatus is advantageous over the other schemes of apparatuses, in terms of scattered-ray removal capability, economy and so on. For this reason, the most of the X-ray CT apparatuses currently in service employ the R-R scheme.

However, there are technical difficulties unique to the R-R scheme. For example, sampling pitch (ray interval) is fixed by an arrangement pitch of the detector elements, thus disabling free control. Consequently, where sampling is not sufficiently fine, the problem of aliasing takes place. There is a practical difficulty in detector element arrangement with sufficient density because incurring the problems of lowered X-ray detection efficiency resulting from the interval of detector elements (dead zone) and of cost. For this reason, the R-R-schemed X-ray CT apparatus can be considered always exposed to the danger of artifact due to aliasing.

As a measure against this, a Q-Q (Quarter-Quarter) offset method (called Quarter-offset method, offset detector or the like) is employed as described in JP-A-53-126892 (Japanese Patent Application No. Sho-52-41666) and a paper "Peters T M and Lewitt R M: Computed Tomography with Fan Beam Geometry. J Comput Assist Tomogr, Vol. 1, No. 4, 1977, 429-436".

According to the Q-Q offset method, the X-ray tube and the detector are oppositely arranged such that the ray closest to a rotation center upon rotation of the X-ray tube and the X-ray detector deviates (offsets) by a quarter of sampling pitch (pitch projected of a detector element pitch onto a vicinity of the rotation center) Δ from the rotation center. Due to this, the ray on each view is to sneak through between the rays of the immediately opposite views, thus enabling to effectively reduce the sampling pitch down to a half (see FIG. 9A in the later).

However, it is not practically easy to arrange the X-ray tube and the X-ray detector in a manner correctly securing the quarter-pitched offset amount based on the Q-Q offset method.

One of the reasons is because there is variation in the positional relationship between an X-ray tube housing and a focal point. During manufacture, alignment is carefully done on each X-ray tube. However, this is impossible to a perfect. Another reason lies in that the most of the X-ray CT apparatuses use an X-ray tube having two focuses large and small in size. In this case, generally the two focuses cannot be placed at the same point, i.e., usually several millimeters of positional error exists between the both focuses. Accordingly, alignment is done at one focus while the other focus (mostly, large focus) deviated from the QQ state (i.e., state correctly secured with a quarter-pitched offset amount based on the Q-Q offset method) is to be compromisingly used in scanning with thick slicing, e.g., 5 mm and 10 mm. With thick slicing, partial volume effect acts in the Z-axis direction and suppresses the high-frequency component of projection data, making aliasing not so conspicuous.

However, the problem of aliasing is in a tendency toward re-actualization due to the recent spread of multi-slice CT. There is currently spread of multi-slice CTs with 8 and 16 rows. For such a CT, scanning by thin slicing is quite common. Moreover, in order to supplement photon deficiency in thin slicing, there is a tendency of carrying out a scanning with the large focus even at a slicing of as small as 1-2 mm, thereby securing a dose. In this case, because such a thin slice is scanned in a state departed from the QQ state, there arises again a problem of artifact caused by aliasing on the reconstructed image.

In this manner, where adopting the Q-Q offset method, the problem of aliasing occurrence is again actualized due to the recent spread of multi-slice CTs. Thus, there is an urgent need for resolving the problem of aliasing caused on the R-R scheme by means of another approach than the Q-Q offset method.

SUMMARY OF THE INVENTION

The present invention has been made in order to overcome such a current situation in the prior art, and it is an object thereof to enable X-ray CT suppressed or eliminated in the occurrence of R-R-schemed aliasing by another approach than the Q-Q offset method.

The present inventor has conducted an approach to the problem of aliasing from a viewpoint quite different from the conventional in view of the problems involved in the prior art, and found that the problem of aliasing is to be eliminated by that, "in the case of carrying out a scanning departed from a QQ state, an optimal backprojection offset is adopted suited for such a departure state". Namely, it has been found that, where projection data includes a deviation from a desired alignment state due to a misalignment on the detector system, it is effective in aliasing suppression and resolving power maintenance to implement a backprojection to a position suitably offset correspondingly to the misalignment state instead of using a backprojection as per the projection path.

Namely, on principle, as shown in FIG. 1, discrete projection data $p_s(t)$ is assumably obtained by sampling, at a pitch $\Delta$ and offset $\alpha$, a true value $p(t)$ of projection data on a view at a certain projection angle. This is regarded as have been obtained at an offset $\gamma$ and served for image reconstructing operation. Conventionally, it is a practice to backproject a convolution result of such discrete projection data $p_s(t)$ to a position of the offset $\alpha$ (hereinafter, referred to as "sampling offset" as required) (this is referred to as "standard method"). In the present invention, reconstruction process is carried out to make a backprojection to a position shifted by a variable constant value $\gamma$ (hereinafter, referred to as "backprojection offset, as required) without performing such a reconstruction by the standard method.

An X-ray CT apparatus of one aspect of the present invention includes: an X-ray source for irradiating an X-ray; an X-ray detector arranged with a plurality of X-ray detector elements and for detecting the X-ray; a rotating unit configured to rotate the X-ray source and the X-ray detector; a collecting unit configured to cause the X-ray detector to collect the X-ray irradiated from the X-ray source; and a reconstructuring unit configured to perform a backprojection operation on projection data based on an output signal of the X-ray detector and to reconstruct an image, wherein the rotating unit is structured such that an X-ray path closest to a rotation center of upon rotation of the X-ray source and the X-ray detector is in a position deviated by a first value $\alpha_d$ from the rotation center, and the to reconstruct unit is structured such that, upon the backprojection operation, the projection data at least in a vicinity of the rotation center is backprojected to a position deviated by a second value $\gamma_d$ different from the first value $\alpha_d$ from the rotation center so as to reduce an artifact level.

An X-ray CT apparatus of another aspect of the present invention includes: a detector system oppositely arranged with an X-ray source for irradiating an X-ray and an X-ray detector arranging a plurality of X-ray detector elements, by sandwiching a subject; a scanning unit configured to cause the X-ray source to irradiate an X-ray on each view while rotating the X-ray source and the X-ray detector in unison round the subject, and the X-ray detector to collect as collected data transmission data of the X-ray to the subject; and a reconstructing unit configured to process the collected data on each view to thereby obtain projection data and to perform a backprojection operation on the projection data to thereby reconstruct an image, wherein the reconstructing unit is configured such that, when the X-ray detector element closest to a rotation center of the detector system is in a position where an X-ray path, taking the irradiated X-ray detection, deviates by a first value $\alpha_d$ from the rotation center, projection data of the X-ray detector element at least in a vicinity of the rotation center upon the backprojection operation is backprojected to a position deviated by a second value $\gamma_d$ different from the first value $\alpha_d$ from the rotation center so as to reduce an artifact level.

An X-ray CT apparatus of another aspect of the present invention includes: an X-ray source for irradiating an X-ray; an X-ray detector arranged with a plurality of X-ray detector elements and for detecting the X-ray; a rotating unit configured to rotate about a rotation center the X-ray source and the X-ray detector in a state opposed to each other; a collecting unit configured to cause the X-ray detector to collect the X-ray irradiated from the X-ray source: and a reconstructing unit configured to perform a backprojection operation on projection data based on an output signal of the X-ray detector and to reconstruct an image, wherein the reconstructing unit is configured such that, when the X-ray detector element closest to a rotation center of the detector system is in a position where an X-ray path, taking the irradiated X-ray detection, deviates by a first value $\alpha_d$ from the rotation center, projection data of the X-ray detector element at least in a vicinity of the rotation center upon the backprojection operation is backprojected to a position deviated by a second value $\gamma_d$ different from the first value $\alpha_d$ from the rotation center so as to reduce an artifact level. An X-ray CT apparatus of another aspect of the present invention comprises: an X-ray source for irradiating an X-ray; an X-ray detector arranged with a plurality of X-ray detector elements and for detecting the X-ray; a rotating unit configured to rotate about a rotation center the X-ray source and the X-ray detector in a state opposed to each other; a collecting unit configured to cause the X-ray detector to collect the X-ray irradiated from the X-ray source; and a reconstructing unit configured to perform a backprojection operation on projection data based on an output signal of the X-ray detector and to reconstruct an image, wherein the rotating unit is structured such that an X-ray path closest to the rotation center of upon rotation of the X-ray source and the X-ray detector is in a position deviated by a first value $\alpha_d$ from the rotation center; and the reconstructing unit is structured to make a backprojection operation to at least a vicinity of the rotation center on a basis of an assumption that the rotation center has a deviation amount of a second value $\gamma_d$ different from the first value $\alpha_d$ so as to reduce an artifact level.

Meanwhile, an X-ray CT backprojection operating method of one aspect of the present invention is a backprojection operating method carried by an X-ray CT apparatus including a detector system oppositely arranged with an X-ray source for irradiating an X-ray and an X-ray detector arranging a plurality of X-ray detector elements by sandwiching a subject, includes: a scanning step of causing the X-ray source to irradiate an X-ray on each view while rotating the X-ray source and the X-ray detector in unison round the subject, and the X-ray detector to collect collected data as transmission data of the X-ray to the subject; and a reconstructing step of processing the collected data on each view to thereby obtain projection data and making a backprojection operation on the projection data to thereby reconstruct an image, wherein, as for the backprojection operation carried out by the reconstructing step, when the X-ray detector element closest to a rotation center of the detector system is in a position where an X-ray path, taking the irradiated X-ray detection, deviates by a first value $\alpha_d$ from the rotation center, projection data of the X-ray detector element at least in a vicinity of the rotation center upon the backprojection operation is backprojected to a position deviated by a second value $\gamma_d$ different from the first value $\alpha_d$ from the rotation center so as to reduce an artifact level.

BRIEF DESCRIPTION OF THE DRAWINGS

In the accompanying drawings:

FIG. 1 is a figure explaining a sampling offset and backprojection offset related to the principle of the present invention;

FIG. 2 is a figure of a frequency transfer function described for explaining the principle of the invention;

FIG. 3 is a figure showing a simulation result described for explaining the principle of the invention;

FIG. 4 is a figure showing a quantitative comparison of a mean artifact level described for explaining the principle of the invention;

FIG. 9 is a figure explaining an arrangement example of an X-ray source and a detector;

DETAILED DESCRIPTION OF PREFERRED EMBODIMENTS

Figure 5:
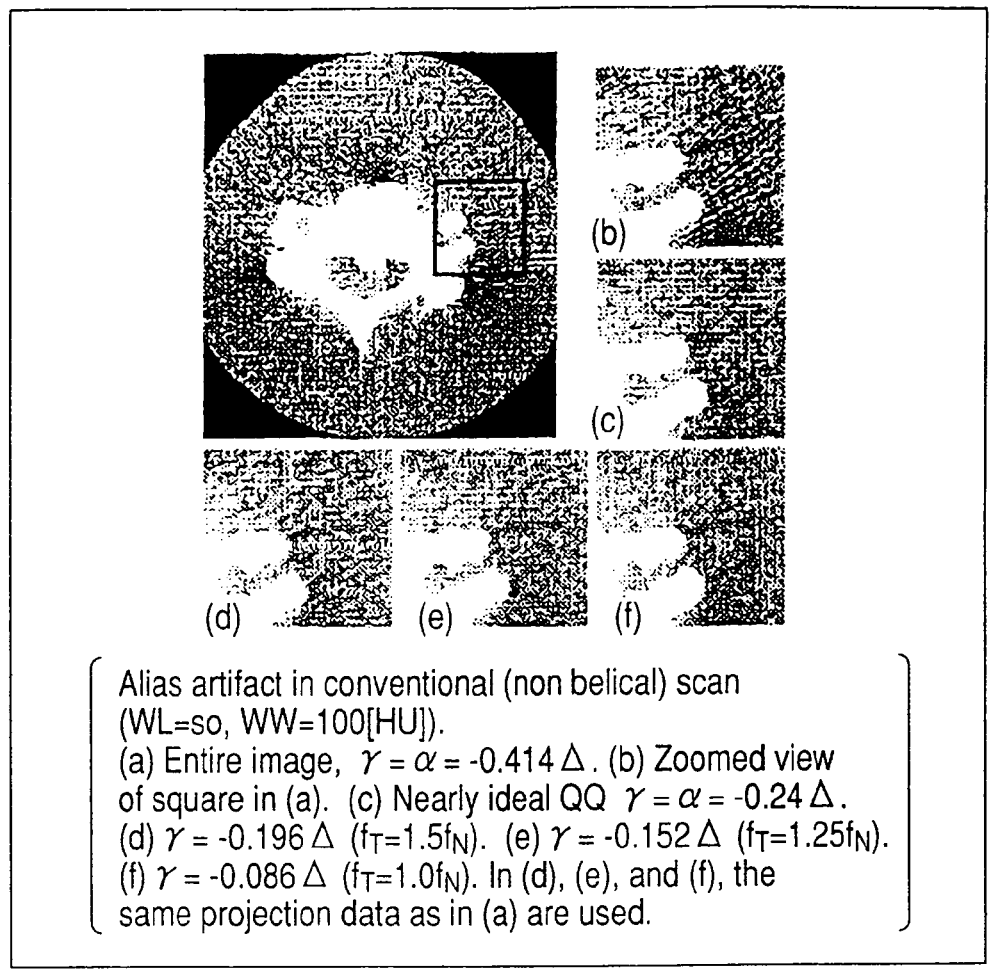
FIG. 5 is a figure showing an experimental result described for explaining the principle of the invention.

Explanation is now made on an embodiment of an X-ray CT apparatus and X-ray-CT backprojection operating method according to the present invention.

At first, explanation is made on the outline of a study result of a backprojection operating method conducted by the present inventor upon configuring the present invention, along with a result of simulation. Although the detailing of theory deduction is omitted, the outline thereof is as follows.

The X-ray beam irradiated from an X-ray tube, neglected as a fan beam, is approximated as a collimated beam. This works well if not far from a rotation center.

Consideration is made on the behavior of a pair of views of projection data in a relationship opposite to each other. It is assumed that one of the views has a sampling offset=α and a backprojection offset=γ while the other view has those of α' and γ'. In case a spectrum in a sum of the both is considered, it can be expressed with approximation by the following equations. In the following equations, p(t) is a true value of projection data, P(f) is a Fourier transform of p(t) i.e., a true spectrum, $P_s s(t)$ is a function that p(t) is shifted to a γ position, and $P_s s(f)$ is a Fourier transform of $P_s s(t)$.

$$P_{sum}(f) = \frac{1}{2}\{P_{sS}(f) + P'_{sS}(f)\} \quad (1)$$

$$\approx \frac{1}{\Delta}\left\{P\left(f - \frac{1}{\Delta}\right)A_1 + P(f)A_0 + P\left(f + \frac{1}{\Delta}\right)A_{-1}\right\}$$

$$A_1 = \frac{1}{2}\left\{\cos\left(k + \frac{2\pi\alpha}{\Delta}\right) + \cos\left(k' + \frac{2\pi\alpha'}{\Delta}\right)\right\} - \quad (2)$$

$$i\frac{1}{2}\left\{\sin\left(k + \frac{2\pi\alpha}{\Delta}\right) + \sin\left(k' + \frac{2\pi\alpha'}{\Delta}\right)\right\}$$

$$A_0 = \frac{1}{2}\{\cos(k) + \cos(k')\} - i\frac{1}{2}\{\sin(k) + \sin(k')\} \quad (3)$$

$$A_{-1} = \frac{1}{2}\left\{\cos\left(k - \frac{2\pi\alpha}{\Delta}\right) + \cos\left(k' - \frac{2\pi\alpha'}{\Delta}\right)\right\} - \quad (4)$$

$$i\frac{1}{2}\left\{\sin\left(k - \frac{2\pi\alpha}{\Delta}\right) + \sin\left(k' - \frac{2\pi\alpha'}{\Delta}\right)\right\}$$

$$k = 2\pi f(\gamma - \alpha) \quad (5)$$
$$k' = 2\pi f(\gamma' - \alpha')$$

$A_1, A_0$ and $A_{-1}$ can be regarded as the respective frequency transfer functions of an aliasing on the positive frequency side, an original spectrum and an aliasing on the negative frequency side. Accordingly, by selecting γ and γ', the respective frequency transfer functions can be put under control.

$$|A_1| = |\cos(2\pi f(\gamma-\alpha) + \pi(\alpha-\alpha')/\Delta)| \quad (6)$$

$$A_0 = \cos(2\pi f(\gamma-\alpha)) \quad (7)$$

$$|A_{-1}| = |\cos(2\pi f(\gamma-\alpha) - \pi(\alpha-\alpha')/\Delta)| \quad (8)$$

In case a restriction γ'−α'=−(γ−α) is introduced from the consideration not to cause positional deviation in a reconstructed image, γ is obtained as follows that satisfies $|A_1|=0$ at a particular frequency $f_T$ (>0) from the equation (6).

$$\gamma = \alpha - (\alpha - \alpha')/2f_T\Delta - (2m+1)/4f_T \quad (9)$$

Here, m is an arbitrary integer. By selecting such γ, the aliasing component in the vicinity of $f_T$ is intensively suppressed. Aliasing must be similarly suppressed in also the negative frequency region, the γ selection in nature satisfies $|A_{-1}|=0$ as well at $f=-f_T$ due to the symmetry of the equation.

Although there are uncountable number of γ satisfying equation (9) because of arbitrariness of m, the optimal selection of m is to minimize |γ−α|. Incidentally, Round means the nearest integer value.

$$m_{opt} = \text{Round}\left[-\frac{\alpha - \alpha'}{\Delta} - \frac{1}{2}\right] \quad (10)$$

The reason of selecting such m and γ as to minimize |γ−α| is that $A_0$ must keep a high value in a region up to high frequency region from a viewpoint at first of MTF. It is of greater importance that $|A_1|$ and $|A_{-1}|$ must keep values of close to zero over a possible broader frequency region about $f_T$ and $-f_T$ respectively, in order for effective aliasing suppression. However, according to equations (6) and (8), such bandwidth is inversely proportional to |γ−α|.

In conclusion, in case γ is selected as in the following, aliasing spectrum can be suppressed over a broad range by substituting to $f_T$ a center of a desired spatial frequency band.

$$\gamma_{opt} = \alpha - \frac{\alpha - \alpha'}{2f_T\Delta} - \frac{1}{4f_T}(2m_{opt} + 1) \quad (11)$$

In the case that there is no variation in sampling offset during scanning, i.e., provided that the rotary gantry is rigid wherein there is no variation in X-ray focal point, no instability in detector mounting and no displacement of rotary center, then α'=−α is held for the opposite views. This simplifies the selecting equation for proper γ and the frequency transfer function thereof. In the following, such a system is handled in the embodiment.

$$m_{opt} = \text{Round}\left[-\frac{2\alpha}{\Delta} - \frac{1}{2}\right] \quad (12)$$

$$\gamma_{opt} = \alpha - \frac{\alpha}{f_T\Delta} - \frac{2m_{opt} + 1}{4f_T} \quad (13)$$

$$|A_1| = \left|\cos\left(2\pi f(\gamma_{opt} - \alpha) + \frac{2\pi\alpha}{\Delta}\right)\right| \quad (14)$$

$$A_0 = \cos(2\pi f(\gamma_{opt} - \alpha)) \quad (15)$$

$$|A_{-1}| = \left|\cos\left(2\pi f(\gamma_{opt} - \alpha) - \frac{2\pi\alpha}{\Delta}\right)\right| \quad (16)$$

As apparent from the above, aliasing component can be suppressed in a certain range about a frequency $f_T$ in accordance with γ selection. Conversely, in case determining as to what frequency region is taken as a target for aliasing suppression, it may be taken $f_T$ to thereby determine γ. Although the range of $f_T$ selection has an infinite broadness of from −∞ to +∞, the standard method (γ=α) corresponds to selecting ±∞ as $f_T$, thus rendering $A_1$ flat over the entire region (non-zero excepting under perfect QQ condition). Meanwhile, from a physical intuition, it can be expected that optimal selection is near with $f_T=+1/(2\Delta)$. Namely, the usual projection data has a spectrum attenuating greater at higher frequency. Aliasing contamination is expectedly caused the most readily in the vicinity of the Nyquist frequency. However, it is impossible to simply determine as to where is the best point nearby the Nyquist frequency, from the reasons what form is taken in projection data spectrum for a practical subject on the actual equipment, in what frequency band an artifact is visually concerned about, and so on. Proper selection of $f_T$ requires a final confirmation on the actual equipment.

FIG. 2 shows an example of an original spectrum transfer function $A_0$ and aliasing spectrum transfer function $|A_1|$, $|A_{-1}|$ when $\gamma$ is reasonably selected (at a value possibly not optimal but approximate to it) during a misalignment with a deviation from the QQ condition state. It can be seen that, by a selection of $\gamma$, it works like a notch-filter with respect to the aliasing. Incidentally, in a perfect QQ state, $A_0=1$, $|A_1|=|A_{-1}|=0$ is obtained by providing $\gamma=\alpha$ ($=0.25(2n+1)\Delta$).

The present inventor has confirmed by a simulation and experiment as to in what region the aliasing spectrum is to be suppressed. This is outlined below.

(Simulation)

There is shown in FIG. 3 an example of a part of an image that an elliptic cylinder of scanning data is produced at $\alpha=-0.10\Delta$ by the personal computer and then reconstructed by changing $\gamma$ at an interval of $0.10\Delta$.

The images obtained at various $\gamma$ were removed of phantom structure to leave an artifact component only, followed by being applied by two-dimensional Fourier transform. Integration was made in a rotational direction on each dynamic diameter (spatial frequency) of from the origin, thus obtaining a spectrum distribution of artifact components. The spectrum is averaged over a range of from 0 to a pixel Nyquist frequency (1.6 [lp/mm]) to have a value taken as a mean artifact level (on arbitrary unit). The mean artifact levels at respective $\gamma$ were quantitively compared, a result of which is shown in FIG. 4. From the quantitive result, the best is at $\gamma=-0.40\Delta(f_T=f_N(\text{Nyquist frequency}))$. However, the best was seemed at $\gamma=-0.50\Delta(f_T=0.75f_N)$ by visual observation.

(Experiment)

Scanning was carried out over a human-structured simulation phantom by means of the actual equipment. Image reconstruction was made with $\alpha=-0414\Delta$, at several ones of $\gamma$ nearby $\gamma=-0414\Delta$ (standard method, $f_T=\infty$) and $f_T=f_N=1/(2\Delta)$. FIG. 5 shows the images. In misalignment ($\alpha=-0414\Delta$), the artifact is pronounced in the standard method of FIG. 5B. This can be improved by properly selecting $\gamma$ in FIGS. 5D, 5E and 5F. Among these, FIG. 5E is visually preferred wherein $f_T$ has been selected somewhat higher than $f_N$ ($f_T=1.25 f_N$, $\gamma=-0.152\Delta$). It was found that this has an image quality not inferior to that of under nearly perfect QQ ($\gamma=\alpha=-0.24\Delta$) of FIG. 5C.

From the above, the aliasing suppression band at its center is preferably taken in the vicinity of the Nyquist frequency. However, if precise distinctions are to be pursued, selection is usefully at somewhat higher than the Nyquist frequency. Note that this somewhat differs depending upon a subject and clinical purpose. Furthermore, it presumably differs to a certain extent depending upon image reconstruction condition.

Figure 6:
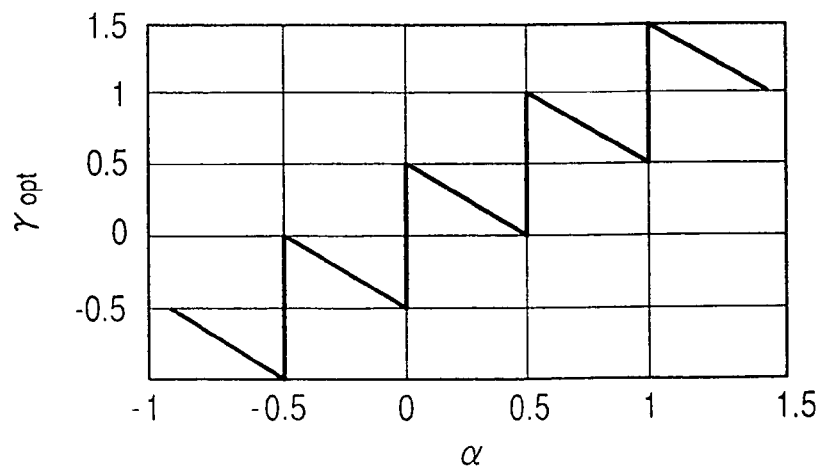
FIG. 6 is a graph representing a proper backprojection offset for various sampling offsets described for explaining the principle of the invention.

Proper $\gamma$ if plotted against a variety of $\alpha$ provides a form as in FIG. 6. This is a determination of $\gamma_{opt}$ at $f_T=f_N=1/(2\Delta)$ from equations (12) and (13) while paying attentions to the Nyquist frequency, because there is intuitively known a difficulty in the vicinity of the Nyquist frequency despite the original spectrum P(f) is indefinite and hence aliasing spectrum distribution is not known. The ordinate is $\gamma_{opt}$ while the abscissa is $\alpha$. Values can be read by magnifying $\Delta$ times on both the ordinate and the abscissa.

In FIG. 6, the vertical line means that the equivalent result is to be obtained even if $\gamma$ is taken at any one of the both ends. It is not allowed to take an intermediate value at other than the both ends of the vertical line.

Figure 7:
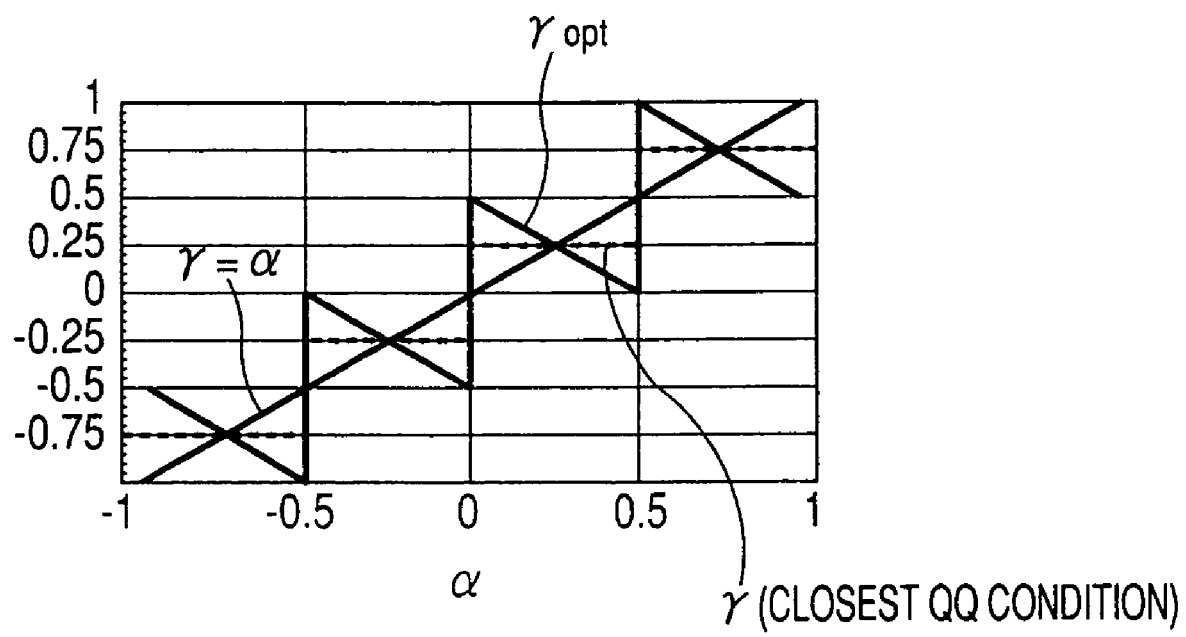
FIG. 7 is another graph representing a proper backprojection offset for various sampling offsets described for explaining the principle of the invention.

Meanwhile, in FIG. 7, the lines based on the standard method ($\gamma=\alpha$) are drawn in addition to FIG. 6 (refer to oblique lines). The closest line in a QQ state is also drawn by a dotted line. The closest signifies a value represented as $(n/2+1/4)\Delta$ when $\alpha$ lies in a range of from $(n/2)\Delta$ to $((n+1)/2)\Delta$ (n is an integer). This is a value of $\gamma$ ($=\alpha$) to be selected at $\alpha=(n/2+1/4)\Delta$, i.e., when perfect QQ alignment is established. Looking at the figure, it is shown that $\gamma$ selection is optimally at a point striding over the $\gamma$ based on the closest QQ condition. Meanwhile, there is shown that leap degree should be increased with the increasing degree of departure of $\alpha$ from the QQ alignment.

Concrete Embodiment

Explanation is now made on a concrete embodiment of an X-ray CT apparatus, on the basis of the above consideration result. Incidentally, in order to show a concrete example, explanation is preferably made differently from the foregoing as to how to take a coordinate system for the sampling offset $\alpha$ and backprojection offset $\gamma$. In order to distinguish it, sampling offset is assumed $\alpha_d$ while backprojection offset is $\gamma_d$.

In the above theoretical explanation, when certain projection data was obtained, sampling axis was defined in direction wherein, even if there was a rotation in measurement system, discussion was made on the former sampling axis. Namely, in case sampling offset $\alpha$ was positive when obtaining certain projection data, sampling offset $\alpha$ when obtaining opposite-sided projection data was in such a direction that $\alpha$ was negative on condition of rotation being stable.

Consequently, in the following explanation, sampling offset $\alpha$ is determined as positive/negative with reference to a measurement system, i.e., detector array. Detector devices in a group are numbered, for example, with j in the order of from one end to the other end. The same direction as numbering of detector devices is taken as an increasing direction of sampling offset $\alpha$. This is true for backprojection offset $\gamma$. The offsets $\alpha$ and $\gamma$ to be handled in this manner are respectively denoted as $\alpha_d$ and $\gamma_d$. The offsets $\alpha$ and $\gamma$ in the foregoing theoretical equations (12)-(16) may be construed $\alpha_d$ and $\gamma_d$ as they are because correctly introduced with the projection data of the opposite view.

Figure 8:
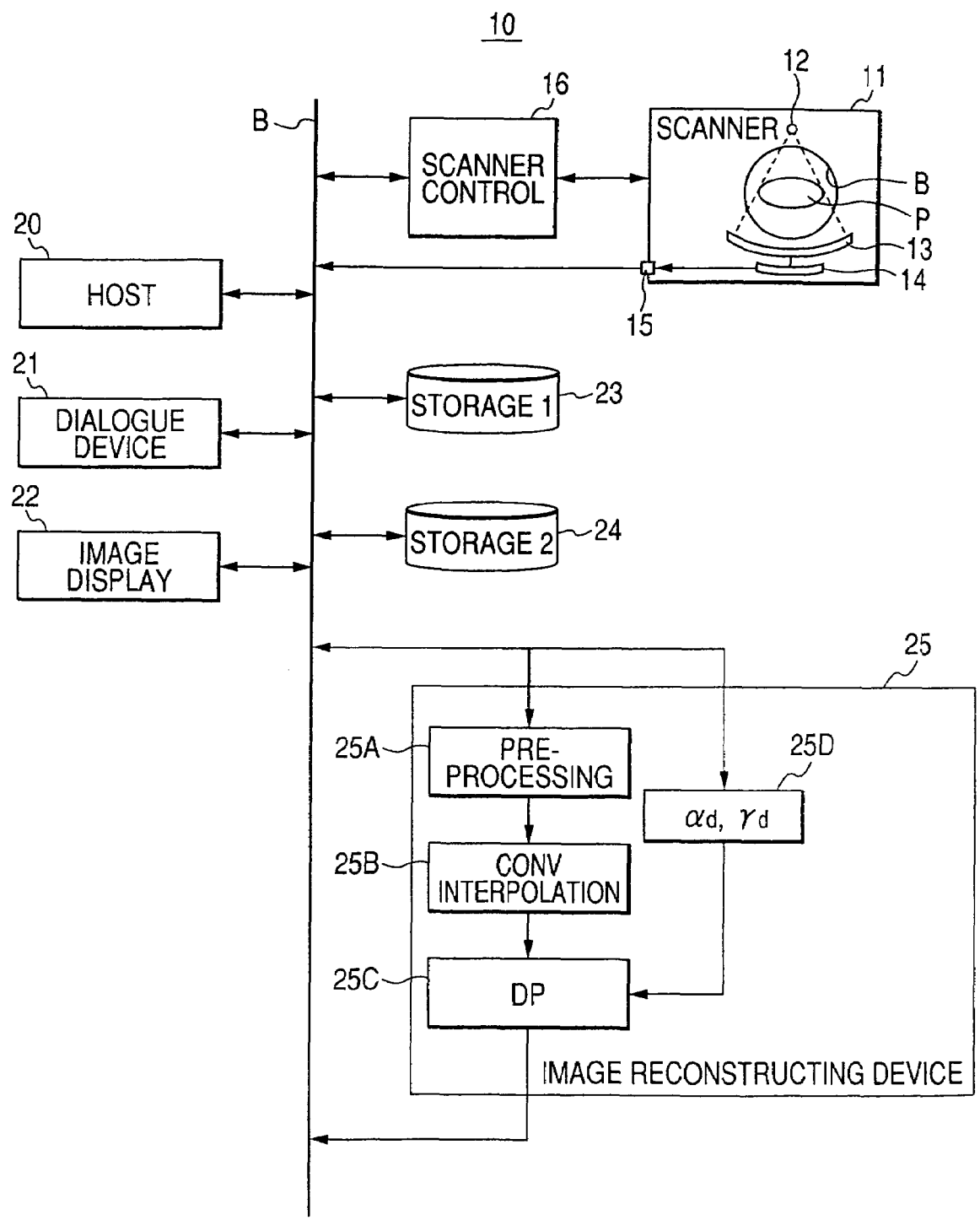
FIG. 8 is a block diagram exemplifying a schematic configuration of an X-ray CT apparatus of the invention.

FIG. 8 shows the outline of a system configuration of an X-ray CT apparatus according to the present embodiment.

As shown in the figure, the X-ray CT apparatus has a CT scanner 10. The scanner 10 has a gantry 11. The gantry 11 has a bore B as a diagnostic space capable of receiving a subject P. The gantry 11 has therein an X-ray tube (X-ray source) 12 and an X-ray detector 13 that are oppositely arranged sandwiching the subject P. The X-ray detector 13 has a plurality of X-ray detector elements in a one-dimensional or two-dimensional arrangement. The X-ray beam irradiated from the X-ray tube 12 and shaped into a fan beam or cone beam transmits to the subject P, to be detected by the detector elements of the X-ray detector 13. The detection signal, in an electric quantity detected by the detector elements of the X-ray detector 13, is converted into X-ray data in digital quantity by a DAS (data collector device) 14. The X-ray data is conveyed as collected data to a fixed-sided bus B through a data transmitter device 15.

The CT scanner 10 operates under control of the scanner control section 16 that receives a control signal and drive signal through the bus B. The scanner control section 16 takes a supply control of a high voltage for a person to be exposed by an X-ray to the X-ray tube 12, a rotation control of the rotary part of the gantry 11 and a behavior control of a diagnostic table (not shown) for resting a subject P thereon. This makes it possible to carry out an R-R-schemed scanning and collect projection data of the subject P.

The bus B is connected with a host computer 20, a dialogue device 21, a display device 22, first and second storage devices 23, 24, and an image reconstructing device 25, as shown in the figure.

The host computer 20 administers the system overall including R-R-schemed scanning operation. The dialogue device 21 has input devices such as a manipulator, enabling the operator to input required information. The display device 22 is used when the operator interactively manipulates the system, besides displaying a reconstructed image.

The first and second storage devices 23, 24, although configured by a storage device such as a magnetic disk, may be configured by partitioning the same medium for use. Of these, the first storage device 23 is stored with a system program, a system constant list, a selection table and so on. The second storage device 24 is capable of storing the collected data outputted from the DAS 14, the data processed by a hereinafter-referred pre-processing section, i.e., projection data, and the image data reconstructed as referred later.

The image reconstructing device 25 has functionally a pre-processing section 25A for making various corrections to collected data, a convolution/interpolation section 25B for making a convolution and interpolation on the data corrected by the pre-processing section 25A, i.e., projection data, a backprojection section 25C for carrying out a backprojection operation on the data operated with convolution and interpolation by the convolution/interpolation section 25B, and a storing section 25D storing the foregoing sampling offset $\alpha_d$ and backprojection offset $\gamma_d$ values.

These offset $\alpha_d$, $\gamma_d$ values are delivered from the host computer 21 to the storing section 25D, and temporarily or everlastingly stored in the storing section 25D. During image reconstruction, the backprojection offset $\gamma_d$ value is read out of the storing section 25D and sent to the backprojection section 25C. Accordingly, the backprojection section 25C can carry out a predetermined backprojection operation on the result data of convolution and interpolation operations, by the use of the sent backprojection offset $\gamma_d$.

Explanation is now made on the operation of the X-ray CT apparatus of the invention, centering on setting of offsets $\alpha_d/\gamma_d$ and application of the backprojection offset $\gamma_d$ thereof to backprojection operation.

There is shown in FIG. 9A a desired arrangement example of an X-ray tube 12 as an X-ray source and X-ray detector 13. The crossing line has an intersection that is a rotation center O. However, it is assumed that the X-ray tube 12 and the X-ray detector 13 are actually arranged as shown in FIG. 9B (i.e., X-ray tube 12 (X-ray focal point) and X-ray detector 13 have a geometry deviated from the ideal QQ condition).

Figure 10:
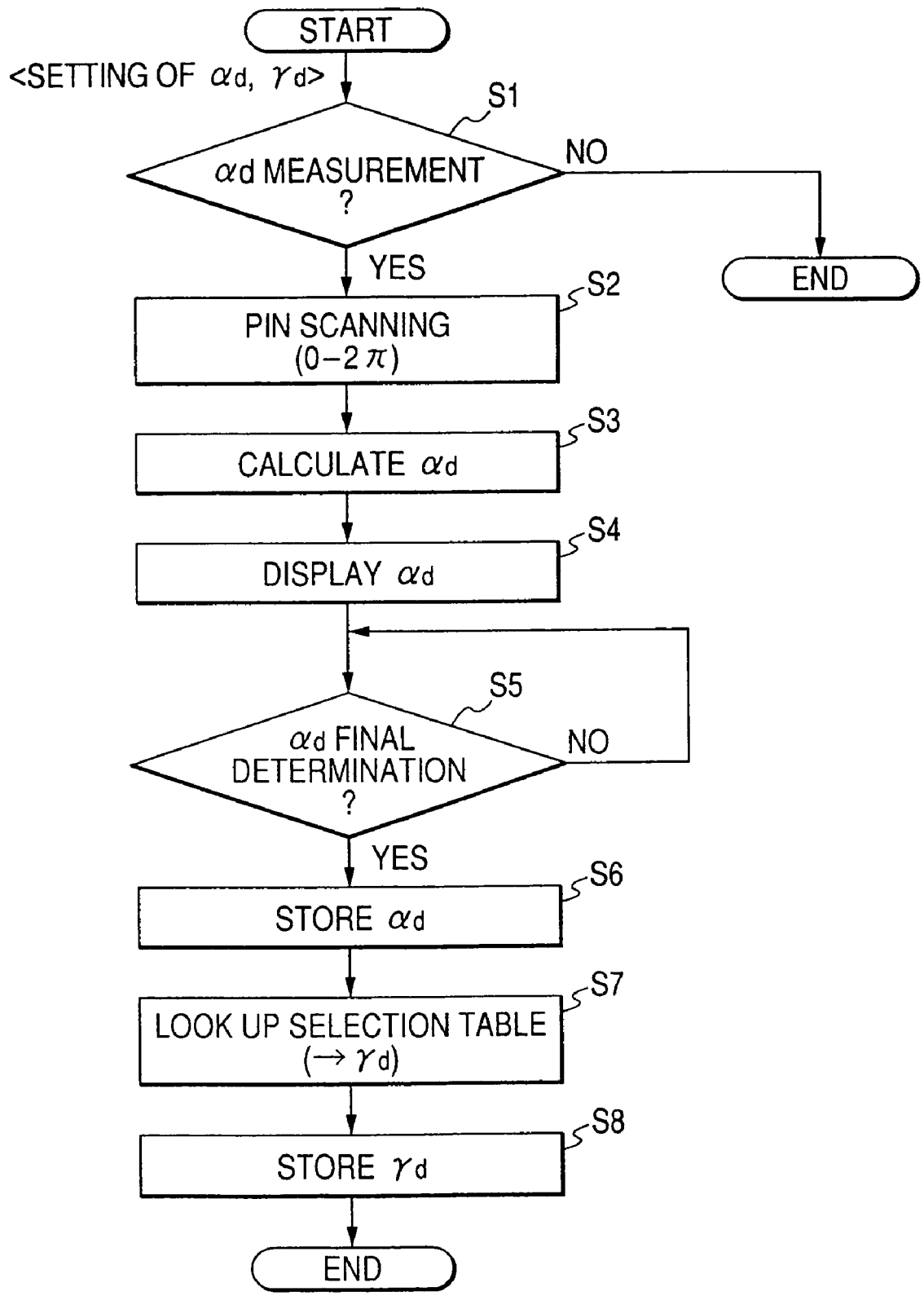
FIG. 10 is a flowchart showing an example of setting process of a sampling offset and backprojection offset to be executed by a host computer.

The host computer 21 executes a setting process of the offsets $\alpha_d$, $\gamma_d$, on the basis of FIG. 10. The setting is usually performed during system adjustment upon installing the X-ray CT apparatus, during focal point adjustment upon exchanging the X-ray tube, during maintenance/regular inspection or the like.

Consequently, the host computer 21, in such an event, supervises whether or not there is an instruction for starting such a setting operation from the operator through the dialogue device 21 (step S1). When it can be determined that such an instruction is made (YES, step S1), processing is made to measure a sampling offset $\alpha_d$ (step S2-S7).

The sampling offset $\alpha_d$ is a value representing how far from a rotation center is distant an X-ray path carried by a detector element numbered j=j$_c$ determined as nearly a center of among the detector elements (numbered j) of the X-ray detector 13 by the system.

For measuring a sampling offset $\alpha_d$, the operator (usually, user or serviceman) sets up a pin at around the rotation center. The coordinate of the same is assumed as x, y. This pin is scanned over a projection angle $\phi=0-2\pi$ (step S2).

Figure 11:
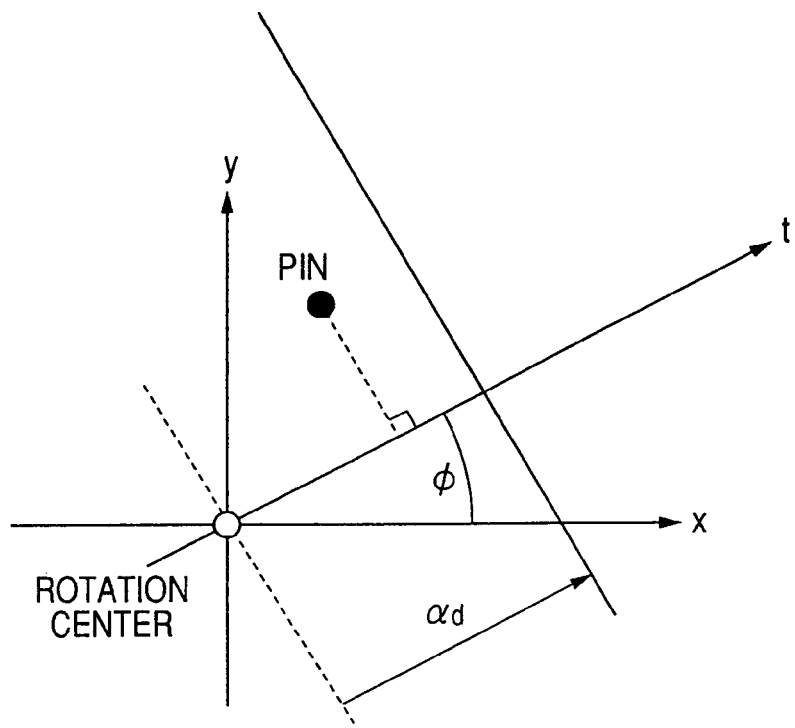
FIG. 11 is a figure explaining a measurement situation of a sampling offset $\alpha$.

As shown in FIG. 11, the coordinate orthogonal to a projection direction is taken as t-axis. The value t at which projection is effected at a pin center is as follows. The system can calculate a center of gravity of a pin shade on each of projection data. The value is assumed j$_p$ (this includes a fraction).

$$t = (j_p - j_c)\Delta + \alpha_d \tag{17}$$

$$t = x\cos\phi + y\sin\phi \tag{18}$$

From this, sampling offset $\alpha_d$ is determined as follows.

$$\alpha_d = x\cos\phi + y\sin\phi - (j_p - j_c)\Delta \tag{19}$$

Because sampling pitch $\Delta$ is not fully fine and there is noise, j$_p$ includes errors. Furthermore, x and y have to be handled as unknown because they could not be positioned so correctly at particular points. For this reason, there is a difficulty in accurately determining a sampling offset $\alpha_d$ from one of projection data by the use of the above equation (19).

Therefore, the following eliminates those problems and makes it possible to determine a more accurate sampling offset $\alpha_d$. In brief, an average is taken over one rotation as to how much a pin projection j$_p$ existing in projection data departs from a centered-element number j$_c$ in the pretext.

$$\alpha_d = \frac{\int_0^{2\pi}(x\cos\phi + y\sin\phi - (j_p - j_c)\Delta)d\phi}{2\pi} \tag{20}$$

$$= \frac{0 + 0 - \int_0^{2\pi}(j_p - j_c)\Delta d\phi}{2\pi}$$

Based on the equation (20), the host computer 20 operates a sampling offset $\alpha_d$ value and displays the value on the display 22 (step S3, S4).

The sampling offset $\alpha_d$ desirably takes a value 0.25$\Delta$+n$\Delta$. When the sampling offset $\alpha_d$ value is unsatisfied, the focal point is re-adjusted. Adjustment when impossible to a perfect is satisfactorily to a value approximate to the same. This finally determines a sampling offset $\alpha_d$ (step S5)

Incidentally, when focal points are in plurality, the final sampling offset $\alpha_d$ value is determined on each focal point.

The host computer 20 takes as a constant the sampling offset $\alpha_d$ of upon ending the measurement and automatically stores it to the first storing device 23 (step S6). Incidentally, the user at the end of this operation may input the final sampling offset $\alpha_d$ as a final value through the dialogue device 21.

In this embodiment, the state of FIG. 9B is the final wherein sampling offset $\alpha_d$ assumably revealed as $\alpha_d=+0.40\Delta$.

Next, a value of backprojection offset $\gamma_d$ is established. In this embodiment, the host computer 20 is adapted to automatically determine a backprojection offset $\gamma_d$. Namely, although it is useful to set $f_T$ at or around a Nyquist frequency as stated before, the X-ray CT apparatus of this embodiment has a contrivance to easily determine a backprojection offset $\gamma_d$ from a sampling offset $\alpha_d$ without being conscious especially of such $f_T$ setting.

Specifically, used is a selection table (storage table) previously stored in the first storing device 23. The selection table is previously described with various values of sampling offset $\alpha_d$ and the corresponding values of backprojection offset $\gamma_d$. Accordingly, by designating one sampling offset $\alpha_d$, the corresponding value of backprojection offset $\gamma_d$ can be determined unambiguously.

There is a possibility that the optimal backprojection offset $\gamma_d$ somewhat vary with respect to the same sampling offset $\alpha_d$, depending upon clinic purpose or image reconstructing condition. For this reason, even for the same value of sampling offset $\alpha_d$, this embodiment is adapted to select/set an optimal value from a plurality of values of backprojection offset $\gamma_d$ depending upon a scanning condition, e.g., slice thickness, or an image reconstructing condition, e.g., convolution function.

Thus, the host computer 20 looks up the selection table stored in the first storage device 23 and selects an optimal value of backprojection offset $\gamma_d$ corresponding to the measured sampling offset $\alpha_d$ and suited for a scanning condition and reconstructing condition (step S7). The set backprojection offset $\gamma_d$ value is stored to the first storing device 23 (step S8).

It is now assumed that selected from the selection table is a backprojection offset $\gamma_d$ corresponding to setting an aliasing suppression center to a vicinity of a Nyquist frequency. (In most cases, this sets a backprojection offset $\gamma_d$ approximate to the best). In this case, in case a sampling offset is $\alpha_d=+0.40\Delta$, then setting is made as backprojection offset $\gamma_d=+0.10\Delta$.

In this manner, even on a detection system the X-ray tube 12 (X-ray focal point) and X-ray detector 13 have a geometry deviated from the ideal QQ condition as shown in the above FIG. 9B, it is possible to establish an optimal backprojection offset $\gamma_d$ of the invention easily and simply.

Subsequently, explanation is made on the process of upon backprojection with reference to FIGS. 12 and 13.

When the subject P is scanned by the R-R scheme, the collected data gathered by the scanning is temporarily stored to the second storing device 24. Meanwhile, the sampling offset $\alpha_d$ and backprojection offset $\gamma_d$ set as above are stored in the first storing device 23.

Figure 12:
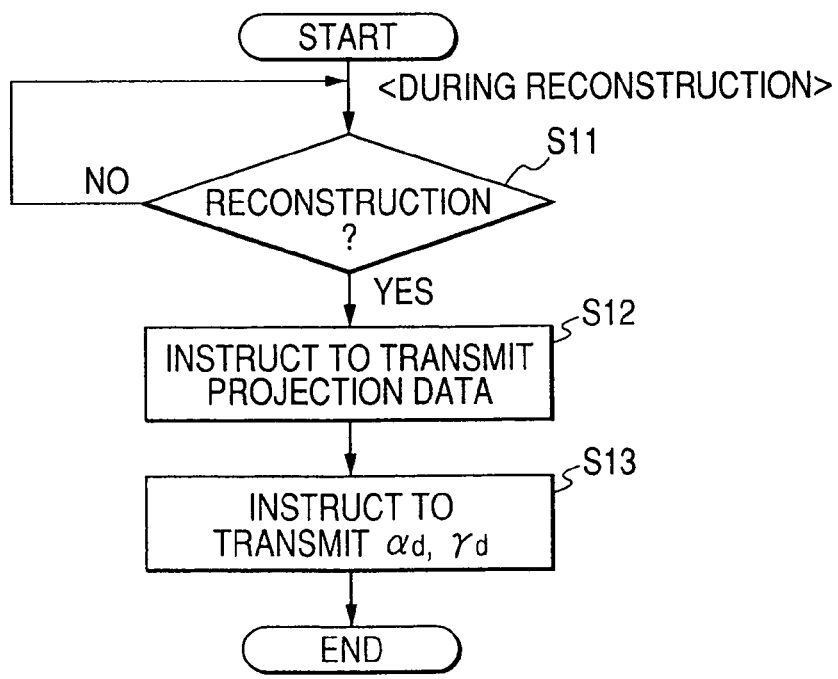
FIG. 12 is a flowchart showing an example of a process during reconstruction to be executed by the host computer.

Thus, the host computer 20 determines whether or not to make a reconstruction depending upon an instruction of the operator sent from the dialogue device 21 (step S11, FIG. 12). When reconstruction is instructed, the process of step S12 and the subsequent is carried out.

Specifically, the host computer 20 delivers the collected data to the pre-processing section 25A of the image reconstructing device 25 (step S12). In this case, the pre-processing section 25A may be notified of an address of the collected data of within the second storing device 24, to allow the second storing device 24 to access the pre-processing device 25A. Similarly, the host computer 20 delivers the sampling offset $\alpha_d$ and backprojection offset $\gamma_d$ to the storing section 25D of the image reconstructing device 25 (step S13). In this case, the storing section 25D may be notified of an address of within the first storing device 23, to allow the first storing-device 23 to access the storing section 25D.

Due to this, the image reconstructing device 25 makes a reconstruction process on the given collected data while taking account of the sampling offset $\alpha_d$ and backprojection offset $\gamma_d$. Namely, various corrections are made to the collected data by the pre-processing section 25A. The corrected data, i.e., projection data (stored as required in the second storing device 24) is then subjected to a convolution and interpolation process by the convolution/interpolation section 25B. Then, the backprojection section 25C makes a backprojection operation on the convolution-operated, interpolation-operated data, along an X-ray path according to the sampling offset $\alpha_d$ and backprojection offset $\gamma_d$.

Figure 13:
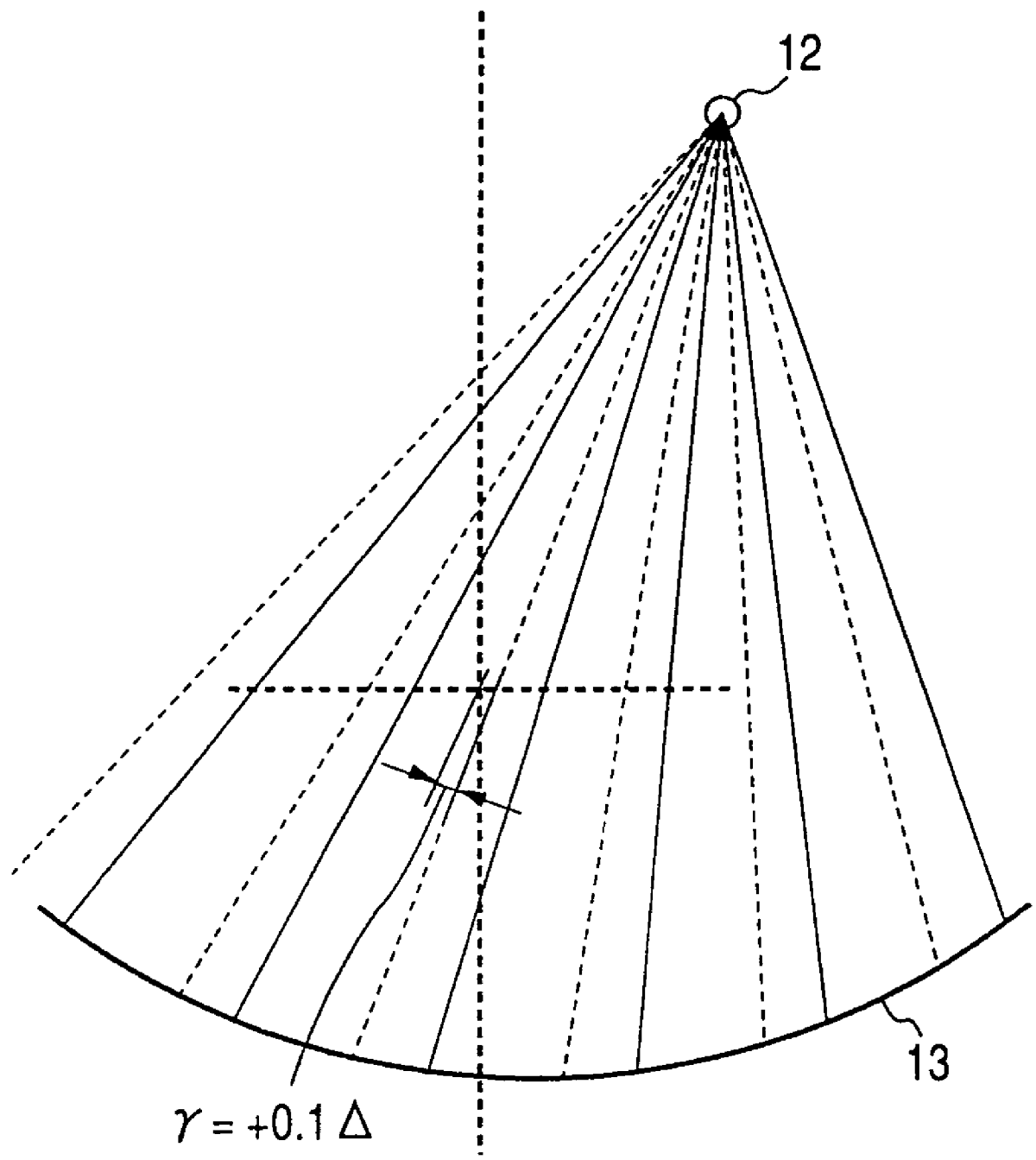
FIG. 13 is another figure explaining an arrangement example of the X-ray source and the detector.

The backprojection is most desirably carried out as shown in FIG. 13. In the figure, the solid line is an X-ray path of actual data collection while the dotted line is a path to backproject the data. The host computer 20 or image reconstructing device 25 can recognize a true X-ray source position because of having measured a sampling offset $\alpha_d$. With the true X-ray source position taken as a start point, backprojection is made based on a designated backprojection offset $\gamma_d$. The centered detector element $j_c$ deviates in an amount corresponding to the backprojection offset $\gamma_d$ while the data of the other detector elements j all offsets the same amount.

This makes it possible to obtain an image less in compensation for blur and fully suppressed in aliasing artifact.

The X-ray CT apparatus and X-ray CT backprojection operation method of the invention are not limited to the arrangement of the above embodiment but can be modified in various ways. Representative ones of such modifications are listed in the following.

(Modification 1)

This modification 1 concerns another manner of how to determine a sampling offset $\alpha_d$.

In place of the pin, scanning is to a wire. From the projection data obtained in the scanning, the backprojection offset $\gamma_d$ is changed to various values to thereby form a plurality of images, thus measuring a PSF (Point Spread Function) at the wire part. By examining the image the sharpest in PSF or a wire CT value peak, recognition may be made such that the backprojection offset $\gamma_d$ presenting an image highest in the peak provides $\alpha_d$. The process and control required can be executed by the host computer 20.

(Modification 2)

This modification 2 concerns another example about indication and notation of sampling offset $\alpha_d$.

The sampling offset $\alpha_d$ may be indicated in value itself, or in value the value $\alpha_d$ is divided by a sampling pitch $\Delta$. This is true for the backprojection offset $\gamma_d$, wherein indication may be in value that offset amount $\gamma_d$ is divided by a sampling pitch $\Delta$. The process needed can be executed by the host computer 20.

Furthermore, notation may be provided to what detector element number j irradiation is made through the X-ray path passing the rotation center, i.e., one-rotation average (with a fraction) of $j_p$ indicated as an actual centered element number, to there by project the data of the $j_x$-numbered ($j_x$ has a fraction) detector element onto the rotation center. This value resultingly handles the same information as offset $\alpha_d$ or $\gamma_d$.

(Modification 3)

This modification 3 shows another manner of how to determine a backprojection offset $\gamma_d$. This is a technique to determine a backprojection offset $\gamma_d$ in a state the sampling offset $\alpha_d$ is unknown.

Even if a sampling offset $\alpha_d$ value cannot be measured, the actually scanned data is applied by a backprojection offset $\gamma_d$ with an interval of "0.05Δ" whereby this value is changed in a certain range thereby reconstructing the image. From among a plurality of images prepared, the operator selects an image whose artifact is suppressed the most. The control in series required can be executed by the host computer 20.

Concerning the image selection, where scanning a subject simple in form, by removing a subject structure and spectrum-analyzing the remaining part, artifact spectrum intensity can be known. Thus, preferably selected is such a backprojection offset $\gamma_d$ that reduces its spectrum mean level or peak level. This calculation is executed by the host computer 20.

On this occasion, the wire is included in the subject to be scanned in order not to select an image conspicuous in compensation for spatial resolving power, thereby simultaneously presenting the PSFs (point image response functions) in the wire part. The operator is required to select the nearest to an offset $\gamma_d$ sharpest in PSF, from the backprojection offsets $\gamma_d$ small in artifact level. This can be automatically implemented by the host computer 20. The image thus selected is made based on a backprojection offset $\gamma_d$ nearly equivalent to that of the image based on a backprojection offset $\gamma_d$ selected with known $\alpha$ and $f_T$.

Furthermore, the operator may input to the system the fact the image has been selected, or input to the system a backprojection offset $\gamma_d$ value as a selection value the system has displayed together with an image.

(Modification 4)

This modification 4 also shows other various ways of how to determine a backprojection offset $\gamma_d$.

The first technique concerns a rough technique to determine a backprojection offset $\gamma_d$ on the premise of a known sampling offset $\alpha_d$. This technique is rough but simple without requiring arithmetic operation formula. At any way, after knowing a sampling offset $\alpha_d$, it is inputted to the backprojection offset $\gamma_d$ at a point somewhat leaping beyond the nearest backprojection offset $\gamma_d$ under QQ condition. The host computer 20 satisfactorily accepts and stores the input. The operator may have a "$\alpha_d$-$\gamma_d$" correspondence table for coping therewith, to make a setting in that way, or make such a setting by a somewhat perception. There is no need to compute a backprojection offset $\gamma_d$ with especial accuracy. If excessive in degree, there is a possibility to raise conspicuous image blur (in compensation for spatial resolving power) with rather worsened aliasing. As a criterion, in case selecting a value at a point somewhat leaping beyond the nearest backprojection offset $\gamma_d$ under QQ condition, there is less possibility of encountering such a disadvantage.

As another approach, the information representative of e.g., what times the Nyquist frequency the $f_T$ should be set may be set as a system constant. In this case a backprojection offset $\gamma_d$ can be determined from equation (13). The host computer 20 determines a backprojection offset $\gamma_d$ by such computation, instead of using a selection table for determining a backprojection offset $\gamma_d$ from a sampling offset $\alpha_d$. By confirmer's key input of the $f_T$, a backprojection offset $\gamma_d$ may be determined.

In this case, the calculation based on equation (13) may be not by the host computer 20 but manual using an electronic calculator or the like by the operator, the result of which may be inputted through the dialogue device 21. The host computer 20, upon calculation based on equation (13), does not require quite the same operation as equation (13) and explicit description as $f_T$. For a versatility of $\alpha_d$, simulation or experiment may be conducted as to what $\gamma_d$ is optimal. From a result of this, a convenient equation may be prepared to select preferable $\gamma_d$ from $\alpha_d$.

Furthermore, determining a backprojection offset $\gamma_d$ may be entrusted to the operator (confirmer) instead of the system. The confirmer can input $f_T$, which is equivalent to a determination of $\gamma_y$.

Otherwise, the confirmer, instead of determining $f_T$, etc., may look at a selection table representative of a relationship of previously prepared offsets $\alpha_d$ and $\gamma_d$ and thereby input an optimal backprojection offset $\gamma_d$.

In order to set an optimal backprojection offset $\gamma_d$ in this manner, the system (host computer 20) may carry out it by operation or looking up a selection table, or otherwise the operator (confirmer) may perform it by an electronic calculator or a quick reference.

Incidentally, sampling offset $\alpha_d$ or properly set backprojection offset $\gamma_d$ may be attached as supplementary information to collected data. Otherwise, the projection data attached with $\alpha_d$ or $\gamma_d$ as supplementary information may be delivered, in this case, to the convolution/interpolation section 25B in FIG. 8 by skipping over the pre-processing section 25A in FIG. 8. In both cases, when used in image reconstruction, the image reconstructing device 25 can carry out an image reconstruction under an optimal condition while making reference to the attached information.

(Modification 5)

This modification 5 concerns a configuration not to directly provide backprojection offset $\gamma_d$ to the image reconstructing device 25.

In the foregoing embodiment, a sampling offset $\alpha_d$ and backprojection offset $\gamma_d$ are provided to the image reconstructing device 25. Alternatively, $\alpha_d$ and $f_T$ are provided to the image reconstructing device 25, from the values of which the image reconstructing device 25 itself may calculate a backprojection offset $\gamma_d$.

(Modification 6)

This modification 6 shows another example of how to reconstruct an image.

In the case of exact reconstruction as shown in the above FIG. 13, backprojection calculation is complicated. Consequently, in case backprojection calculation is made by using only a backprojection offset $\gamma_d$, it is possible to somewhat simplify how to make a backprojection. In this case, the host computer 20 may deliver the image reconstruction device 25 with only a backprojection offset $\gamma_d$ without handing a sampling offset $\alpha_d$. Otherwise, while the host computer 20 may deliver both offsets $\alpha_d$, $\gamma_d$ to the image reconstructing device 25, the device 20 may use only the backprojection offset $\gamma_d$.

In this manner, even if a backprojection offset $\gamma_d$ only is used without knowing a sampling offset $\alpha_d$, it is possible to obtain a sufficiently favorable image in its own way. In this case, aliasing suppression gives an unfavorable result at around a large field of view. However, because aliasing suppression is not so important at around the large field of view, it can be served for use in its own way.

Figure 14:
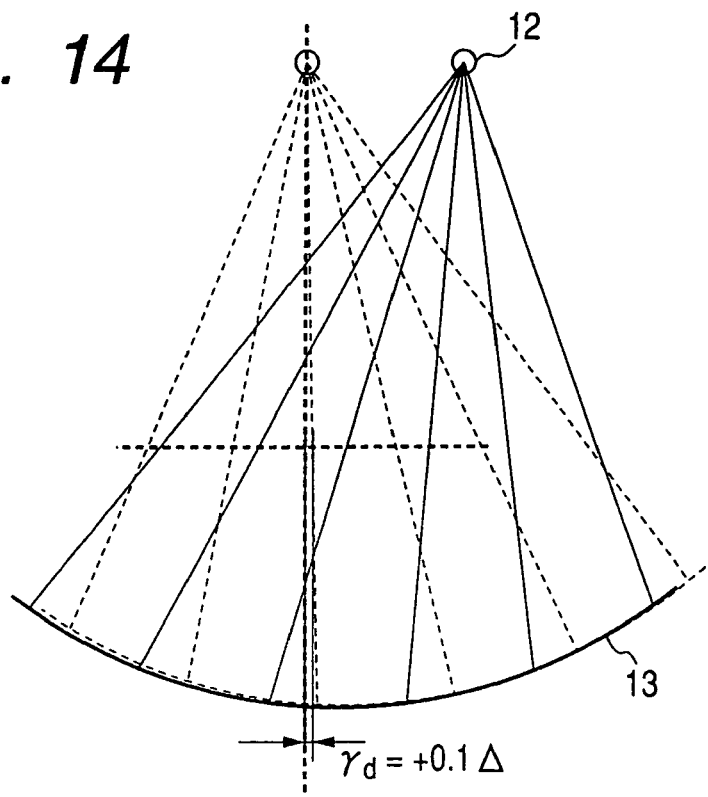
FIG. 14 is another figure explaining an arrangement example of the X-ray source and the detector.

Explanation is made on one simple backprojection operation using solely the above backprojection offset $\gamma_d$, with reference to FIG. 14. The image reconstructing device 25 regards the X-ray source as in a predetermined correct position (position in FIG. 9A). The group of detectors only is given a backprojection offset $\gamma_d$ in a translational direction. Due to this, backprojection is done by regarding the detectors in group as arranged such that the data of the $j_c$-numbered detector element deviates by $\gamma_d$ in the center of the field of view (may be regarded as a deviation in any of lateral and rotational directions, because of slight in quantity).

Figure 15:
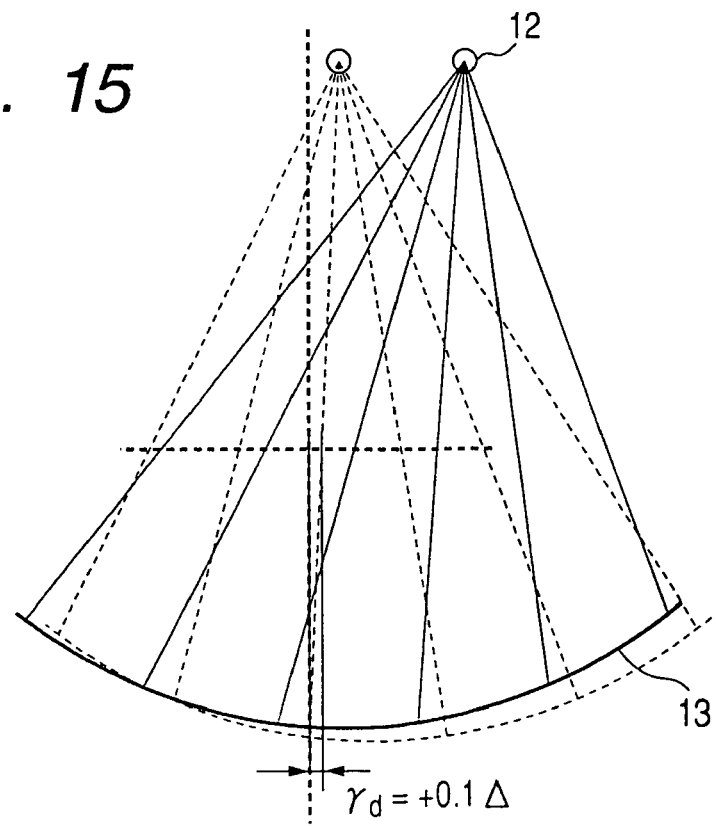
FIG. 15 is another figure explaining an arrangement example of the X-ray source and the detector.

Explanation is made on another simple backprojection operation, by using FIG. 15. The X-ray source and detector group shown in FIG. 15 are regarded as arranged in a predetermined correct position as shown in FIG. 9A. However, with respect to a rotation center, it is handled as somewhat deviated in a translational direction. Translation is in a degree that the data of the $j_c$-numbered detector element deviates $\gamma_d$ in the center of the field of view, i.e., $\gamma_d-(-\Delta/4)$ as compared to FIG. 9A. In this manner, backprojection is implemented by regarding the X-ray source and the detector group as arranged in a pair.

In this manner, backprojection may be done with data deviated a desired degree at around the center of the field of view with respect to a position in acquisition.

(Modification 7)

This modification 7 is an example coping with the case of inaccurate rotation of the rotary member of the gantry 11 supporting the X-ray tube 12 and X-ray detector 13.

Even where there is no variation in sampling offset during scanning, i.e., even when the premise is not held that "the rotary member of the gantry 11 is rigid and free of X-ray focal point variation and detector attaching instability and of rotational center displacement", aliasing artifact can be suppressed.

In this case, there is a need to know a change in sampling offset $\alpha_d$ during rotation. Provided that the above premise is held, $j_p$ relative to $\phi$ behaves as a sinusoidal wave having a particular phase and amplitude in accordance with a pin position. Consequently, in case the path of $j_p$ is subjected to fitting with a sinusoidal wave, the deviation between $j_p$ path and obtained sinusoidal wave represents a variation of sampling offset $\alpha_d$ during rotation.

In case the variation in sampling offset $\alpha_d$ is reproducible, the foregoing equations (10), (11) are usable. However, these equations are rewritten, as a coordinate system given with reference to the detector string as in the following, into equations (21), (22). The value $\alpha_d'$ is a sampling offset of a view immediately opposite to the relevant view.

By knowing $\alpha_d$ and $\alpha_d'$ as a backprojection offset to the relevant view, image reconstruction may be made based on a backprojection offset of nearly $\gamma_{dopt}$.

$$m_{opt} = \text{Round}\left[-\frac{\alpha_d + \alpha_d'}{\Delta} - \frac{1}{2}\right] \quad (21)$$

$$\gamma_{dopt} = \alpha_d - \frac{\alpha_d + \alpha_d'}{2f_T\Delta} - \frac{1}{4f_T}(2m_{opt} + 1) \quad (22)$$

In this case, backprojection offset $\gamma_d$ must be handled as a value changing on a view-by-view basis (or on a view group basis). In the storing section 25D in FIG. 8, sampling offset $\alpha_d$ is stored as a value changing depending upon a view angle $\phi$.

In implementing it, there is a possibility that $m_{opt}$ in equation (21) increment in numeral in the course during a change in view angle. This is not preferable in respect of image quality. In order to make $m_{opt}$ in a fixed value during reconstruction of one image, it is suitable for $\alpha_d$ (or $\alpha_d'$) in equation (21) to employ a mean value of during one rotation.

As in the above, according to the X-ray CT apparatus and X-ray CT backprojection operating method in this embodiment concerns an X-ray CT appartatus for obtaining an image about an internal structure of a subject from collected projection data. This can eliminate the recent problem of aliasing suppression sought for the X-ray CT apparatus for executing scanning based on the R-R scheme, to enhance the quality of an X-ray CT image and contribute to the development in medical industry along with the accuracy improvement in image diagnosis. Namely, where adopting the Q-Q offset method, it is possible to reduce or eliminate the problem of aliasing occurrence actualized along with the recent spread of multi-slice CT.

(Supplementation)

Supplementary explanation is now made on a general guide for selecting a proper backprojection offset $\gamma$ against an arbitrary sampling offset $\alpha$ explained in the foregoing embodiment.

For the foregoing case of FIGS. 6 and 7, it is not easy to grasp what degree it worsens in what degree departed from the guideline and how good when nearby the guideline. Here, such a matter is shown in a visual way. This makes it possible to broadly grasp in what range a desired backprojection offset $\gamma$ is to be selected or in what degree of backprojection offset $\gamma$ a result disadvantageously comes conversely.

The figure shown herein is an extended version of FIG. 4B. FIG. 4B shows a graph of "aliasing degree" in the image that the backprojection offset $\gamma$ is changed for a particular sampling offset $\alpha$. In this term, "aliasing degree" is shown in a shades-of-color diagram by a broad combinations of offsets $\alpha$ and $\gamma$. Although there is arbitrariness in assessing the "aliasing degree", aliasing intensity here assumably has been integrated over a broad range of frequency similarly to FIG. 4B. Although the integration value in FIG. 4B lies in a range of from frequency 0 to 1.8 times the Nyquist frequency, it herein is assumably from 0 to twice the Nyquist frequency (because aliasing concentrates nearby the nyquist frequency, difference is slight in each of the assessments). Meanwhile, as an aliasing degree" index, by a concentration on a particular frequency instead of an integration of aliasing intensity over a broad range, assessment can be made with a target at a frequency 1.25 times or 1 time the Nyquist frequency. In this case, a preferable backprojection offset $\gamma$ somewhat deviates as compared to the case using an index with an integration of aliasing intensity over a broad range. However, in this case, such deviation is also small because of the same reason that aliasing concentrates at nearby the Nyquist frequency. Because the showing here is in a broad aspect, such a deviation is assumed not problematic.

FIG. 4B is an empirical determination. However, experiment is difficult to apply for a broad range of combinations of offsets $\alpha$ and $\gamma$. Hence, it is theoretically determined. Such a theory is detailed in the Document "Medical Imaging Technology Vol. 21 No. 4 Sep. 2003 (Hereinafter, referred to as "this document")". More correctly, disclosed in this document is a theoretical formula (represented by a function T ($\alpha$, $\gamma$, f) in this document) for determining, at each frequency, an aliasing intensity with an arbitrary backprojection offset $\gamma$ against an arbitrary sampling offset $\alpha$. Here, the aliasing intensity thus determined is integrated in a direction of frequency, to obtain "aliasing degree". Meanwhile, in the case of the theory shown in this document, a simple sharp edge is assumed as a subject structure attributable for aliasing, hence making it impossible to perfectly describe on every subject. However, this document confirms that the aliasing behavior sought by such a theory is well matched to that of simulation experiment.

Figure 16:
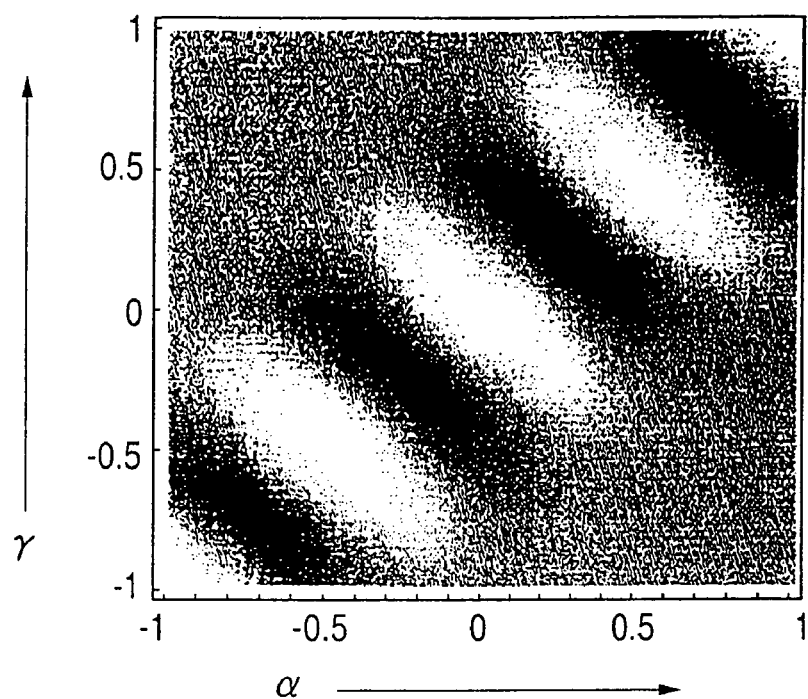
FIGS. 16-19 are figures for supplementary explanation on the general guideline for selecting a proper backprojection offset γ for an arbitrary sampling offset α.
Figure 17:
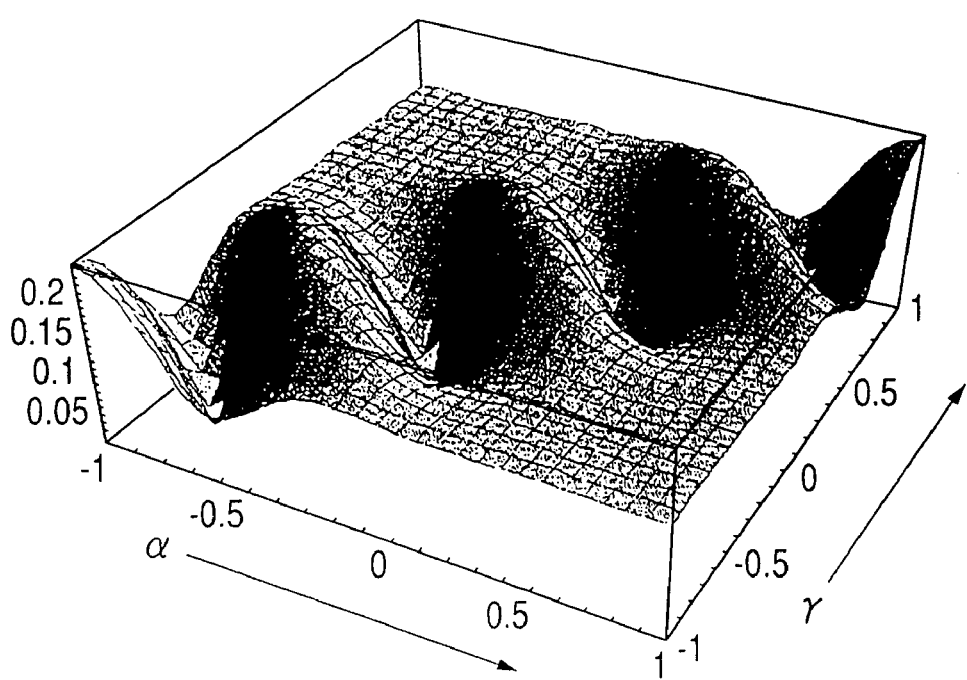

The above determination provides a graph shown in FIG. 16. FIG. 17 is a three-dimensional plotting version of the graph of FIG. 16. This can visually show an aliasing degree in every combination of offsets $\alpha$ and $\gamma$. It would be naturally presumable at an outside of the plotting range. The offset values of α and γ are values normalized at a sampling pitch Δ.

Figure 18:
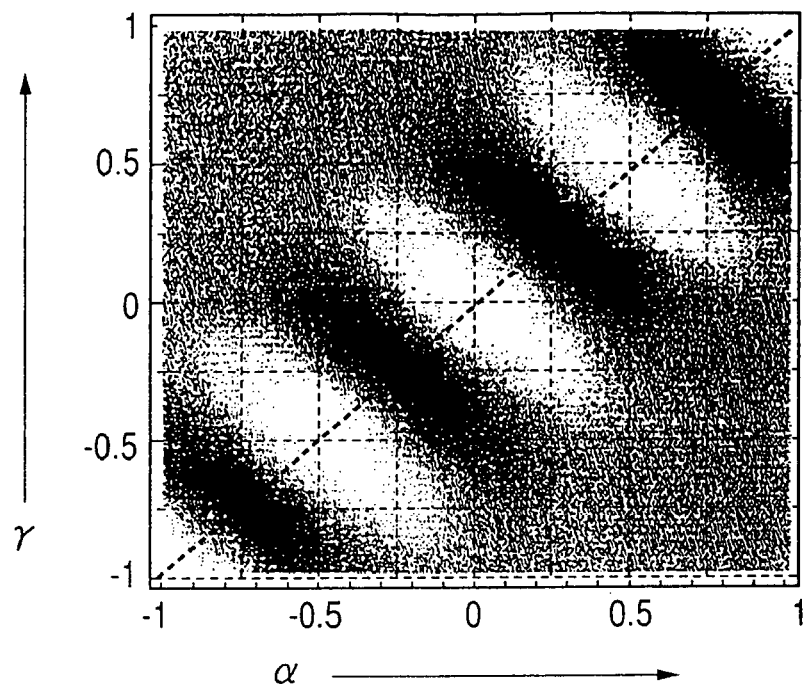

FIG. 18 is an addition of an explanatory auxiliary line (oblique bold line) to FIG. 16. Although FIGS. 16 to 18 are all the same, explanation below is based on FIG. F in the below.

In the standard method, the backprojection offset γ to be taken for each sampling offset α is shown by the oblique bold line. Under the condition other than QQ, aliasing is not minimal. When the sampling offset α deviates 0.25Δ from the QQ condition, selection is the worst, i.e., aliasing greatest in intensity.

For example, observed is the case with an arbitrary sampling offset α=−0.1Δ. In this case, where the backprojection offset γ is brought toward the smaller than −0.1Δ (toward the positive), alias gradually decreases. Conversely, when the backprojection offset γ is brought toward the greater than −0.1Δ (toward the positive), alias gradually increases. Namely, this means that it should be neared to the closest QQ state (γ=−0.25Δ), as noted before. The best selection is at around γ=−0.4Δ. Namely, there exists the best selection at a point striding across the closest QQ state. In case backprojection offset γ is further shifted toward the negative, aliasing gradually increases again. If it is further shifted toward the negative, it passes a weak peak and, ultimately, gradually approaches a constant value.

A criterion is sought of up to what degree of backprojection offset γ usefulness is to be offered. From this FIG. 18, alias apparently increases if excessive. The backprojection sound γ significant in the invention lies in a range where aliasing weakens rather than in the conventional method in FIG. 18. The range would be determined by observing FIG. 18. However, it is difficult to show literally or by equation up to what degree it is effective, by the use of this FIG. 18 only. Nevertheless, the criterion that nothing is available when going to at least such a point can be computed by other calculation.

This calculation formula is shown in equation (23). FIGS. 16-18 have been sought by putting a multiplicity of modification factors to the equation (23). Among those, equation (23) represents the greatest dominant factor. By the use of equation (23), it is possible to obtain a rough criterion of whether a backprojection offset γ having nothing available or a backprojection offset γ having usefulness in FIG. 18 or the like.

$$|A_1|=|\cos(2\pi f(\gamma_{opt}-\alpha)+2\pi\alpha/\Delta)| \quad (23)$$

Here, the target frequency (i.e., frequency of interest) is narrowed down to the Nyquist frequency (1/(2Δ)).

In the conventional method, aliasing at the Nyquist frequency is given as follows.

$$\text{Juurai}=|\cos(2\pi\alpha/\Delta)| \quad (24)$$

The optimal assumably lies at a certain γ=γopt. The aliasing at that time at the Nyquist frequency is as follows.

$$\text{Saiteki}=|\cos(2\pi 1/2\Delta(\gamma_{opt}-\alpha)+2\pi\alpha/\Delta)|$$

Because the frequency of interest is narrowed down to the Nyquist frequency, γopt is given as the following value.

$$m_{opt} = \text{Round}\left[-\frac{2\alpha}{\Delta}-\frac{1}{2}\right] \quad (25)(=\text{equation }12)$$

$$\gamma_{opt} = \alpha - \frac{\alpha}{f_T\Delta} - \frac{2m_{opt}+1}{4f_T} \quad (26)(=\text{equation }13)$$

$$= \alpha - \frac{1}{2}(1+2m_{opt})\Delta$$

Here, the following value is assumed as a further excessive backprojection offset γ.

$$\gamma_{far}=\gamma_{opt}+(\gamma_{opt}-\alpha) \quad (27)$$

Figure 19:
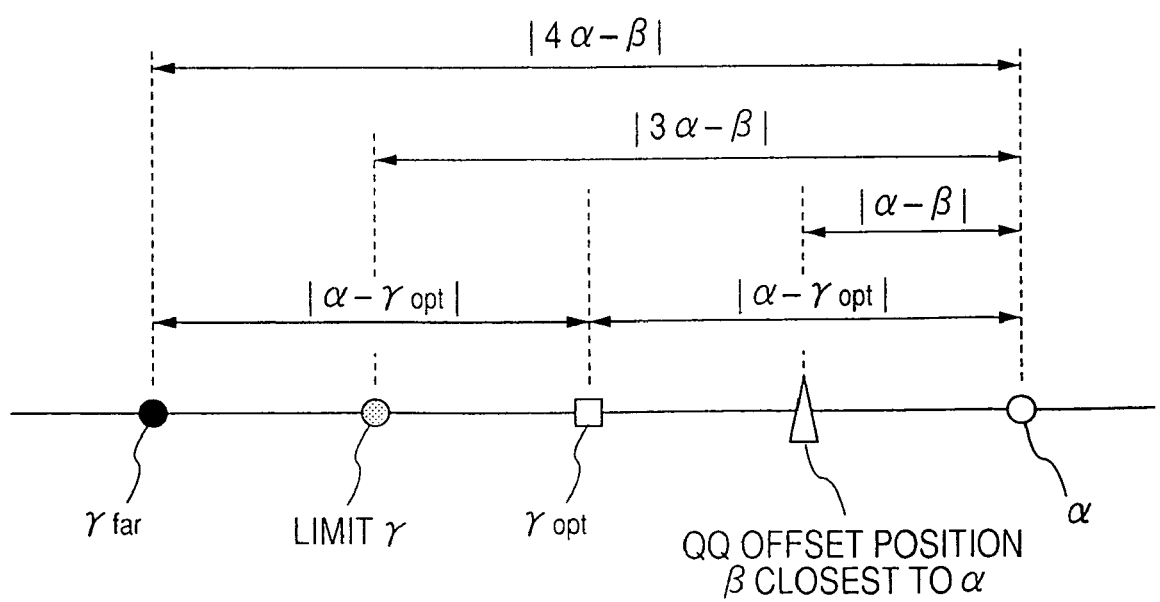

This provides a positional relationship as shown in FIG. 19. The aliasing (at the Nyquist frequency) at this time is given as follows.

$$\text{far}=|\cos(2\pi 1/2\Delta(\gamma_{far}-\alpha)+2\pi\alpha/\Delta)| \quad (28)$$

By doing so, the following is held for every sampling offset α though concrete calculation is omitted.

$$\text{far}=\text{Juurai} \quad (29)$$

Namely, selection is possible at such γfar that γopt is passed over into a point and aliasing is equal to that in the former conventional method. As for the backprojection offset γ not reaching such a point, aliasing is lower than that of the conventional method.

This γfar, if expressed in words, is as follows. There is a closest QQ offset position β to the sampling offset α. It is advantageous to select a backprojection offset γ at a value closer to β than the sampling offset α. Furthermore, the optimal γ exists at a point beyond β. Further beyond there, such γ that the distance to α is 4 times the distance between α and β is in a point where aliasing suppression function is lost. Selecting γ in this range provides a significance for aliasing suppression.

In the above, the Nyquist frequency was selected as a target frequency. Where taking another frequency as a target, γopt changes in position. However, the γfar in the foregoing positional relationship holds for a relationship far=juurai at every frequency, i.e., the relationship that aliasing in the succeeding does not go below that of the standard method.

Actually, at γfar and the γfarther farer, image aliasing artifact possibly lowers rather than the aliasing in the standard method (γ=α) due to the modification factor of other than equation (23). This would be seen by carefully observing FIG. 18. However, such selection of γ as exceeding γfar signifies a huge |γ−α|. The use of such γ in place of γopt in equation (24) results in excessively great compensation for spatial resolving power (blur). The compensation for spatial resolving power would no longer be neglected in γfar. Selecting γ at distant from the oblique bold line in FIG. 18 increases blur in proportion to the distance. Accordingly, γfar generally must be determined to incur image loss rather than in the former standard method.

Accordingly, in the practical criterion, γ has an upper limit lying not so far as γfar. It cannot be simply determined at what point the limit is placed because of the presence of user's taste. At a point of γ of from α to 3 |α−β|, alias artifact is positively smaller than in the former state. Therefore, the range of |γ−α| not exceeding 3 |α−β| is suitably defined as a practical limit in γselection.

In conclusion, γ selection range practically significant is as follows. There is a closest QQ offset position β to α. γ is selected in value lying in a direction toward β as viewed from α. However, it is within a range that |γ−α| does not exceed 3 |α−β|. More preferably, γ is selected at a point exceeding β. Further preferably, γ is in a position nearly symmetric with α sandwiching β as mentioned in FIGS. 6 and 7.

Further desirably, it is a point slightly closer to α than a point nearly symmetric with α.

Incidentally, although not detailed in FIGS. 6 and 7, the target frequency is preferably selected somewhat higher than the Nyquist frequency. This actually is meant to select γ at slightly closer to α than a point in symmetry with α sandwiching β. In case the target frequency is selected somewhat higher than the Nyquist frequency, then γopt nears some what closer to α than the point in symmetry with α sandwiching β.

What is claimed is:

1. An X-ray CT apparatus comprising:
    an X-ray source for irradiating an X-ray;
    an X-ray detector arranged with a plurality of X-ray detector elements and for detecting the X-ray;
    a rotating unit configured to rotate the X-ray source and the X-ray detector around a subject such that an X-ray path closest to a rotation center of upon rotation of the X-ray source and the X-ray detector is in a position deviated by a first value $\alpha_d$ from the rotation center, and the X-ray path and a longitudinal axis of the subject are substantially perpendicular to each other;
    a collecting unit configured to cause the X-ray detector to collect the X-ray irradiated from the X-ray source;
    a setting unit configured to set a second value $\gamma_d$ in accordance with the first value $\alpha_d$ by looking up a table, including a connection between the X-ray path and a path to backproject projection data based on an output signal of the X-ray detector connected to reduce an aliasing artifact level on an image, and by storing a previous correspondence of the first value $\alpha_d$ and the second value $\gamma_d$, or by operating based on an operation equation, including the connection, defining a relationship between the first value $\alpha_d$ and the second value $\gamma_d$;
    a storing unit configured to store the second value $\gamma_d$ set by the setting unit; and
    a reconstructuring unit configured to perform a backprojection operation on the projection data and to reconstruct the image,
    wherein the reconstructing unit is configured to upon the backprojection operation, backproject the projection data at least in a vicinity of the rotation center to a position deviated by the second value $\gamma_d$ different from the first value $\alpha_d$ from the rotation center so as to reduce an artifact level.

2. An X-ray CT apparatus according to claim 1, wherein the second value $\gamma_d$ at least in a vicinity of the rotation center is a value deviated from the first value $\alpha_d$ in a manner suppressing an aliasing artifact of the image, as compared to a case of backprojection along an X-ray path of upon collecting the X-ray.

3. An X-ray CT apparatus according to claim 2, wherein when a certain value β is used, the second value $\gamma_d$ at least in a vicinity of the rotation center is in a positional relationship to satisfy $\alpha_d > \beta > \gamma_d$ or $\alpha_d < \beta < \gamma_d$, the certain value γ being a value under a QQ (Quarter-Quarter) offset condition closest to the first value $\alpha_d$, which is a value of $n\Delta+\Delta/4$ of upon employing such n as minimizing $|\alpha_d-(n\Delta+\Delta/4)|$ (Δ is a sampling pitch in a vicinity of the rotation center, n is an arbitrary integer).

4. An X-ray CT apparatus according to claim 1, wherein the setting unit takes account of a condition for executing at least one of the collecting unit and the reconstructing unit in addition to the first value $\alpha_d$ and automatically sets the second value $\gamma_d$.

5. An X-ray CT apparatus according to claim 1, further comprising an input unit configured to input the second value $\gamma_d$ from an external of the X-ray CT apparatus, and a storing unit configured to store the second value $\gamma_d$ inputted through the input unit in order to reconstruct the image.

6. An X-ray CT apparatus according to claim 1, further comprising an input unit configured to input information about an aliasing frequency band that is to be desirably suppressed in aliasing artifact on the image, an operating unit configured to operate the second value $\gamma_d$ on a basis of information inputted through the input unit, and a storing unit configured to store the second value $\gamma_d$ operated by the operating unit in order to reconstruct the image.

7. An X-ray CT apparatus according to claim 1, wherein the collecting unit has a scanning unit configured to cause the X-ray source to irradiate an X-ray at each view while rotating the X-ray source and the X-ray detector in unison round the subject, and allowing the X-ray collector to collect transmission data of the X-ray to the subject, the second value $\gamma_d$ being a value to be varied depending upon a projection angle of each view by the collecting unit.

8. An X-ray CT apparatus according to claim 1, further comprising a unit configured to reconstruct and display a plurality of images different in the second value $\gamma_d$ and selecting a desired image from among the plurality of images thereby setting a desired one of the second value $\gamma_d$.

9. An X-ray CT apparatus comprising:
    a detector system oppositely arranged with an X-ray source for irradiating an X-ray and an X-ray detector arranging a plurality of X-ray detector elements, by sandwiching a subject such that an X-ray path closest to a rotation center of upon rotation of the detector system is in a position deviated by a first value $\alpha_d$ from the rotation center, and the X-ray path and a longitudinal axis of the subject are substantially perpendicular to each other;
    a scanning unit configured to cause the X-ray source to irradiate an X-ray on each view while rotating the X-ray source and the X-ray detector in unison round the subject, and the X-ray detector to collect as collected data transmission data of the X-ray to the subject;
    a setting unit configured to set a second value $\gamma_d$ in accordance with the first value $\alpha_d$ by looking up a table, including a connection between the X-ray path and a path to backproject projection data based on an output signal of the X-ray detector connected to reduce an aliasing artifact level on an image, and by storing a previous correspondence of the first value $\alpha_d$ and the second value $\gamma_d$, or by operating based on an operation equation, including the connection, defining a relationship between the first value $\alpha_d$ and the second value $\gamma_d$;
    a storing unit configured to store the second value $\gamma_d$ set by the setting unit; and
    a reconstructing unit configured to process the collected data on each view to thereby obtain the projection data and to perform a backprojection operation on the projection data to thereby reconstruct the image,
    wherein the reconstructing unit is configured such that, the projection data of the X-ray detector element at least in a vicinity of the rotation center upon the backprojection operation is backprojected to a position deviated by the second value $\gamma_d$ different from the first value $\alpha_d$ from the rotation center so as to reduce the aliasing artifact level.

10. An X-ray CT apparatus comprising:
    an X-ray source for irradiating an X-ray;
    an X-ray detector arranged with a plurality of X-ray detector elements and for detecting the X-ray;
    a rotating unit configured to rotate about a rotation center the X-ray source and the X-ray detector in a state opposed to each other around a subject such that an X-ray path closest to a rotation center of upon rotation of the X-ray source and the X-ray detector is in a position deviated by a first value $\alpha_d$ from the rotation center, and the X-ray path and a longitudinal axis of the subject are substantially perpendicular to each other;
    a collecting unit configured to cause the X-ray detector to collect the X-ray irradiated from the X-ray source;

a setting unit configured to set a second value $\gamma_d$ in accordance with the first value $\alpha_d$ by looking up a table, including a connection between the X-ray path and a path to backproject projection data based on an output signal of the X-ray detector connected to reduce an aliasing artifact level on an image, and by storing a previous correspondence of the first value $\alpha_d$ and the second value $\gamma_d$, or by operating based on an operation equation, including the connection, defining a relationship between the first value $\alpha_d$ and the second value $\gamma_d$;

a storing unit configured to store the second value Yd set by the setting unit; and a reconstructing unit configured to perform a backprojection operation on the projection data and to reconstruct the image, wherein the reconstructing unit is configured such that, the projection data of the X-ray detector element at least in a vicinity of the rotation center upon the backprojection operation is backprojected to a position deviated by the second value $\gamma_d$ different from the first value $\alpha_d$ from the rotation center so as to reduce the aliasing artifact level.

11. An X-ray CT apparatus comprising:

an X-ray source for irradiating an X-ray;

an X-ray detector arranged with a plurality of X-ray detector elements and for detecting the X-ray;

a rotating unit configured to rotate about a rotation center the X-ray source and the X-ray detector in a state opposed to each other around a subject such that the X-ray path and a longitudinal axis of the subject are substantially perpendicular to each other;

a collecting unit configured to cause the X-ray detector to collect the X-ray irradiated from the X-ray source;

a setting unit configured to set a second value $\gamma_d$ in accordance with the first value $\alpha_d$ by looking up a table, including a connection between the X-ray path and a path to backproject projection data based on an output signal of the X-ray detector connected to reduce an aliasing artifact level on an image, and by storing a previous correspondence of the first value $\alpha_d$ and the second value $\gamma_d$, or by operating based on an operation equation, including the connection, defining a relationship between the first value $\alpha_d$ and the second value $\gamma_d$;

a storing unit configured to store the second value $\gamma_d$ set by the setting unit; and a reconstructing unit configured to perform a backprojection operation on the projection data and to reconstruct the image, wherein the reconstructing unit is structured to make a backprojection operation to at least a vicinity of the rotation center on a basis of an assumption that the rotation center has a deviation amount of the second value $\gamma_d$ different from the first value $\alpha_d$ so as to reduce the aliasing artifact level.

12. An X-ray CT backprojection operating method carried out by an X-ray CT apparatus including a detector system oppositely arranged with an X-ray source for irradiating an X-ray and an X-ray detector arranging a plurality of X-ray detector elements by sandwiching a subject, comprising:

a scanning step of causing the X-ray source to irradiate an X-ray on each view while rotating the X-ray source and the X-ray detector in unison round the subject such that an X-ray path closest to a rotation center of upon rotation of the X-ray source and the X-ray detector is in a position deviated by a first value $\alpha_d$ from the rotation center, the X-ray path and a longitudinal axis of the subject are substantially perpendicular to each other, and the X-ray detector to collect collected data as transmission data of the X-ray to the subject;

a setting step of setting a second value $\gamma_d$ in accordance with the first value $\alpha_d$ by looking up a table, including a connection between the X-ray path and a path to backproject projection data based on an output signal of the X-ray detector connected to reduce an aliasing artifact level on an image, and by storing a previous correspondence of the first value $\alpha_d$ and the second value $\gamma_d$, or by operating based on an operation equation, including the connection, defining a relationship between the first value $\alpha_d$ and the second value $\gamma_d$;

a storing step of storing the second value $\gamma_d$ set by the setting step; and a reconstructing step of processing the collected data on each view to thereby obtain the projection data and making a backprojection operation on the projection data to thereby reconstruct the image, wherein, as for the backprojection operation carried out by the reconstructing step, the projection data of the X-ray detector element at least in a vicinity of the rotation center upon the backprojection operation is backprojected to a position deviated by a second value $\gamma_d$ different from the first value $\alpha_d$ from the rotation center so as to reduce the aliasing artifact level.

* * * * *